United States Patent [19]

Gaeta et al.

[11] Patent Number: 5,760,062
[45] Date of Patent: Jun. 2, 1998

[54] TELOMERASE INHIBITORS

[75] Inventors: Federico C.A. Gaeta, Foster City; Adam A. Galan, Richmond; Michael R. Kozlowski; Karen R. Prowse, both of Palo Alto; Elaine C. Stracker, Vacaville; Patricia A. Peterli-Roth, Hayward, all of Calif.

[73] Assignee: Geron Corporation, Menlo Park, Calif.

[21] Appl. No.: 425,043

[22] Filed: Apr. 18, 1995

[51] Int. Cl.[6] ................... A61K 31/44; C07D 213/57; C07D 213/84
[52] U.S. Cl. .............. 514/344; 546/288; 546/291; 546/297; 546/298
[58] Field of Search ................ 546/288; 514/344

[56] References Cited

U.S. PATENT DOCUMENTS

| | | | |
|---|---|---|---|
| 4,269,846 | 5/1981 | Huang et al. | 514/363 |
| 4,611,059 | 9/1986 | John C. Sih | 546/281.1 |
| 4,863,923 | 9/1989 | Ho et al. | 514/443 |
| 5,639,613 | 6/1997 | Shay et al. | 435/6 |

FOREIGN PATENT DOCUMENTS

| | | | |
|---|---|---|---|
| 0050957 A1 | 5/1982 | European Pat. Off. | 409/6 |
| 0069521 A2 | 12/1983 | European Pat. Off. | 405/6 |
| 0 158380 B1 | 10/1985 | European Pat. Off. | 333/70 |
| 0483647 A1 | 6/1992 | European Pat. Off. | 333/68 |
| 0512349 A1 | 11/1992 | European Pat. Off. | 333/70 |
| 0568289 A2 | 3/1993 | European Pat. Off. | 333/70 |
| 0572712 A2 | 8/1993 | European Pat. Off. | 333/56 |
| 0619297 A1 | 12/1994 | European Pat. Off. | 237/48 |
| 1927393 | 4/1969 | Germany. | |
| 1936721 | 5/1969 | Germany. | |
| 93/02037 | 4/1993 | WIPO | 53/6 |

OTHER PUBLICATIONS

Nam W. Kim, et al., "Specific Association of Human Telomerase Activity with Immortal Cells and Cancer", Dec. 23, 1994, Science vol. 266 pp. 2011–2014.

Walter Reid, et al., Synthese von substituierten Benzol[b]thiophenen, 1980, Liebigs Ann. Chem pp. 1424–1427.

Steven L. Castle, et al., "The Synthesis of Monomethoxy[1]benzothieno[2,3-c]quinolines", Jul.–Aug. 1987, Department of Chemistry, University of South Florida, pp. 1103–1108. J. Heterocyclic Chem., 24, 1103 (1987).

(List continued on next page.)

*Primary Examiner*—Alan L. Rotman
*Attorney, Agent, or Firm*—David P. Lentini; Kevin R. Kaster

[57] ABSTRACT

Methods and compositions for treating cancer and other diseases in which inhibition of telomerase activity can ameliorate disease symptoms or prevent or treat the disease relate to compounds that are derivatives of pyrido[b]thiophenes, pyrido[b]furans, pyridine ethers or pyridine thioethers. Such compounds are characterized by the following structure:

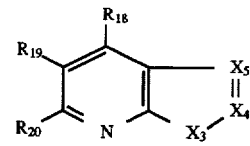

$X_3$ is oxygen or sulfur; and the double dashed lines between $X_4$ and $X_5$ indicate an optional double bond, which, when present, forms a fused, bicyclic pyrido[b]furan or pyrido[b]thiophene ring system, depending upon whether $X_3$ is oxygen or sulfur, respectively. When the double bond is not present, the compound is a monocyclic pyridine ether or thioether, again depending upon whether $X_3$ is oxygen or sulfur. $X_4$ is —$CH_2R_{21}$ or —$CR_{21}$=, where $R_{21}$ is selected from the group consisting of aryl, heteroaryl, aralkyl, heteroaralkyl, alkylcarbonyl, arylcarbonyl, heteroalkylcarbonyl, heteroaralkylcarbonyl, aralkylcarbonyl, aminocarbonyl, alkylaminocarbonyl, arylaminocarbonyl, dialkylaminocarbonyl, diarylarninocarbonyl, arylalkylaminocarbonyl, carboxyl, alkoxycarbonyl, aryloxycarbonyl, sulfo, alkylsulfonyl and arylsulfonyl; and $X_5$ is hydrogen, alkyl, hydroxyl, alkoxyl, aryloxyl, halogen, cyano, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, carboxyl, alkoxycarbonyl, aryloxycarbonyl, sulfo, alkylsulfonyl, arylsulfonyl or —$CR_{22}$= where $R_{22}$ is selected from the group consisting of hydrogen, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, hydroxyl, halogen, cyano, carboxyl, alkoxycarbonyl and aryloxycarbonyl. When $X_4$ is —$CR_{21}$=, $X_5$ is —$CR_{22}$=, and $X_4$ and $X_5$ are joined by the above-mentioned double bond, to form thereby a fused, bicyclic pyrido[b]thiophene ($X_3$ is sulfur) or pyrido[b]furan ($X_3$ is oxygen) ring system. When $X_4$ is —$CH_2R_{21}$, $X_5$ is not —$CR_{22}$=, thereby forming a pyridine ether ($X_3$ is oxygen) or thioether ($X_3$ is sulfur). $R_{18}$ and $R_{19}$ are selected independently from the group consisting of hydrogen, halogen, hydroxy, aryloxy, alkoxy, lower alkyl, aryl, heteroaryl, aralkyl and heteroaralkyl. $R_{20}$ is selected from the group consisting of alkoxymethyl, dialkoxymethyl, arylalkylaminomethyl, arylaminomethyl, alkylaminomethyl, aminomethyl, diarylaminomethyl, dialkylaminomethyl, hydroximinyl, iminyl, aldehyde, alkylcarbonyl, arylcarbonyl, alkyliminyl, aryliminyl, aralkyliminyl, alkoximinyl, aryloximinyl, heterocycleimninyl, alkoxycarbonyl, aryloxycarbonyl, carboxyl, alkene, —HC=NNHR$_{23}$ where R$_{23}$ is selected from the group consisting of hydrogen, alkyl, aryl, aralkyl, heterocycle, heterocyclealkyl, and —C($X_6$)NHR$_{24}$ where $X_6$ is oxygen or sulfur and R$_{24}$ is selected from the group consisting of hydrogen, aryl, arylsulfonyl, aralkyl, heterocycle and heterocyclealkyl.

9 Claims, No Drawings

OTHER PUBLICATIONS

David T. Connor, et al., Novel Benzothiophene–, Benzofuran–, and Naphthalenecarboxamidotetrazoles as Potential Antiallergy Agents, 1992, Journal of Medicinal Chemistry, vol. 35, No. 5.

Tatsuo Higa and Arnold J. Krubsack, Oxidations by Thionyl Chloride. 8. A convenient Synthesis of Benzo[b]thiophenes from Carboxylic Acids and Ketones[1,2], J. Org. Chem., vol. 41, No. 21, 1976.

Tatsuo Higa and Arnold J. Krubsack, Oxidations By Thionyl Chloride. VI. Mechanism of the Reaction with Cinnamic Acids[1,2], 1975, J. Org. Chem. vol. 40, No. 21.

T. de Lange; "Tumor Telomerase"; *Telomeres;* 1995; Cold Spring Harbor Laboratory Press; pp. 284–285.

Kim et al.; "Specific Association of Human Telomerase Activity with Immortal Cells and Cancer" *Science;* vol. 266; 23 Dec. 94; 2011–2014.

TELOMERASE INHIBITORS

NOTICE OF U.S. GOVERNMENT RIGHTS

A portion of the work described herein was funded in part by SBIR Grant No. 1 R43 CA65178-1. The U.S. Government may therefore have certain rights relating to this invention.

BACKGROUND OF THE INVENTION

1. The Field of the Invention

The present invention relates to human telomerase, a ribonucleoprotein enzyme involved in human telomere DNA synthesis, and to compounds that inhibit telomerase activity. The invention provides methods, compounds and compositions relating to the fields of molecular biology, chemistry, pharmacology, oncology and medicinal and diagnostic technology.

2. Description of Related Disclosures

The war on cancer has raged for over two decades. Yet, despite the expenditure of over a billion dollars for research and development of new technologies to diagnose and treat malignancies, the age-adjusted cancer mortality rate in the U.S. has remained largely unchanged for the past forty years. Indeed, if current epidemiological trends continue, it appears likely that cancer will overtake cardiovascular disease as the leading cause of death in the United States.

To be sure, some battles have been won and much has been learned about the enemy. A few cancers (e.g., Hodgkin's disease) are now considered curable, and treatment regimes for many other cancers have improved over the last decade. In addition, there has been an explosion of information describing the regulatory mechanisms involved with the onset of malignancy, including the roles of growth factors, receptors, signal transduction pathways, oncogenes, and tumor suppressor genes in the control of cell growth and differentiation. However, these successes are overshadowed by the fact that cancer is a highly heterogeneous disease in which profound differences exist in the mechanisms by which different cell types become malignant. Thus, although we know more about the mechanisms by which cells become malignant than ever before, each type of cancer presents a unique set of problems in terms of treatment.

Because the cellular mechanisms leading to cancer are so heterogeneous, research on such mechanisms is unlikely to yield a general approach to cancer treatment that is effective and well tolerated by cancer patients. Presently, a variety of non-specific treatment modalities are available, including surgery, radiation, and a variety of cytoreductive and hormone-based drugs, used alone or in combination. Some oncolytic drugs are also available, but the efficacy of these drugs varies among cancer types. Thus, patients suffering from cancer often are forced to undergo treatments that are highly non-specific and highly toxic. Commonly, the toxicity of the treatments produces severe side effects, including nausea and vomiting, hair loss, diarrhea, fatigue, ulcerations and the like, which severely impact the patient's quality of life. In some cases, the impact on the patient's quality of life can be so great that the patient is unable to continue the full course of therapy or opts out of treatment entirely.

Recently, however, an understanding of the mechanisms by which normal cells reach the state of senescence, i.e., the loss of proliferative capacity that cells normally undergo in the cellular aging process, has begun to emerge. The DNA at the ends, or telomeres, of the chromosomes of eukaryotes usually consists of tandemly repeated simple sequences. Scientists have long known that telomeres have an important biological role in maintaining chromosome structure and function. More recently, scientists have speculated that the cumulative loss of telomeric DNA over repeated cell divisions may act as a trigger of cellular senescence and aging, and that the regulation of telomerase, an enzyme involved in the maintenance of telomere length, may have important biological implications. See Harley, 1991, *Mutation Research*, 256:271–282, incorporated herein by reference.

Telomerase is a ribonucleoprotein enzyme that synthesizes one strand of the telomeric DNA using as a template a sequence contained within the RNA component of the enzyme. See Blackburn, 1992, *Annu. Rev. Biochem.*, 61:113–129, incorporated herein by reference. Methods for detecting telomerase activity, as well as for identifying compounds that regulate or affect telomerase activity, together with methods for therapy and diagnosis of cellular senescence and immortalization by controlling telomere length and telomerase activity, have also been described. See Kim, et al., 1994, *Science*, 266:2011–2014; PCT patent publication No. 93/23572, published Nov. 25, 1993; U.S. patent application Ser. Nos. 08/288,501, filed Aug. 10, 1994; 08/330,123, filed Oct. 27, 1994; 08/272,102, filed Jul. 7, 1994; 08/255,774, filed Jun. 7, 1994; 08/315,214 and 08/315,216, both of which were filed Sep. 28, 1994; 08/151,477 and 08/153,051, both of which were filed Nov. 12, 1993; 08/060,952, filed May 13, 1993; and 08/038,766, filed Mar. 24, 1993. Each of the foregoing patent applications and reference is incorporated herein by reference.

The identification of compounds that inhibit telomerase activity provides important benefits to efforts at treating human disease. Compounds that inhibit telomerase activity can be used to treat cancer, as cancer cells express telomerase activity and normal human somatic cells do not express telomerase activity at biologically relevant levels (i.e., at levels sufficient to maintain telomere length over many cell divisions). Unfortunately, few such compounds have been identified and characterized. Hence, there remains a need for compounds that act as telomerase inhibitors and for compositions and methods for treating cancer and other diseases in which telomerase activity is present abnormally. The present invention meets these and other needs.

SUMMARY OF THE INVENTION

The present invention provides methods, compounds and compositions that are highly unique, specific and effective for treating malignant conditions by targeting cells having telomerase activity. The methods, compounds and compositions of the invention can be applied to a wide variety of malignant cell types and avoid the problems inherent in current cancer treatment modalities, which are non-specific and toxic.

In a first aspect, the present invention provides methods and compositions for treating cancer in which a therapeutically effective amount of a benzo[b]thiophene derivative, having the structure shown below, in a pharmaceutically acceptable carrier, is administered to a mammal:

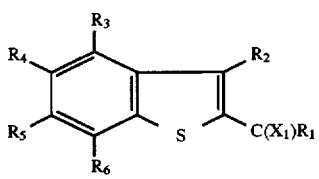

In the structure above, $R_1$ is selected from the group consisting of —$OR_7$, —$NR_8R_9$, —$NHNR_{10}R_{11}$, —NHNHC($X_2$)NHR$_{12}$, —$NHSO_2NR_8R_9$, —NHNHC(O)R$_{12}$, —NHNHSO$_2R_{12}$ and —NHC(O)NR$_8R_9$, where $R_7$-$R_{12}$ are selected independently from the group consisting of hydrogen, alkyl, aryl, aralkyl, heteroaryl and heteroaralkyl. $X_1$ and $X_2$ are selected independently from the group consisting of oxygen and sulfur. Further, in the above structure, $R_2$ is hydrogen or halogen, and $R_3$-$R_6$ are selected independently from the group consisting of hydrogen, halogen, hydroxyl, —$NR_8R_9$, nitro, cyano, alkoxyl, lower alkyl, aryl and aryloxyl.

Preferred benzo[b]thiophene telomerase inhibitors include those in which $R_1$ is —$OR_7$ (with $R_7$ being hydrogen or methyl) or —NHNH$_2$. $R_2$ or $R_6$ is halogen or hydrogen and $R_5$ is alkyl or alkoxyl. Compounds in which $R_2$-$R_4$ are hydrogen, $R_5$ is methyl or methoxy and $R_6$ is chloro, are preferred. Also preferred are compounds in which $R_2$ is chloro, $R_3$ and $R_4$ are hydrogen, $R_5$ is methyl or methoxy and $R_6$ is hydrogen.

Other preferred benzo[b]thiophene derivatives of the present invention are those compounds characterized by $X_1$, being oxygen and $R_1$ (from the above structure) being —NHNHC($X_2$)NHR$_{12}$ where $R_{12}$ is aryl. As noted above, $X_2$ may be oxygen or sulfur. Such compounds have the following structure:

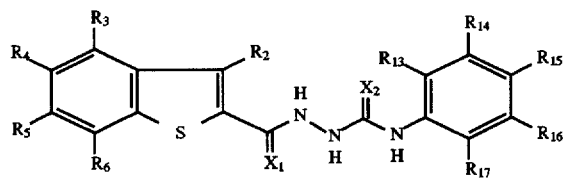

In this structure, $R_{13}$-$R_{17}$ are selected independently from the group consisting of hydrogen, halogen, hydroxyl, nitro, cyano, amino, alkylamino, arylamino, dialkylamino, diarylamino, arylalkylamino, alkoxyl, alkyl, aryl and aryloxyl. Especially preferred derivatives are those in which $X_2$ is sulfur and $R_{13}$-$R_{17}$ are selected independently from the group consisting of hydrogen and chloro.

In another aspect, the present invention provides novel methods, compositions and compounds relating to a class of telomerase inhibiting agents that are derivatives or analogues of fused, bicyclic pyrido[b]thiophenes, pyrido[b]furans, or monocyclic pyridine ethers or pyridine thioethers. These telomerase inhibiting compounds have the general structure shown below:

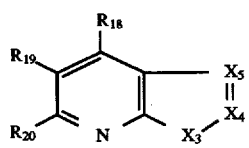

In this structure, $X_3$ is oxygen or sulfur; and the double dashed lines between $X_4$ and $X_5$, indicate an optional double bond, which, when present, forms a fused, bicyclic pyrido[b]furan or pyrido[b]thiophene ring system, depending upon whether $X_3$ is oxygen or sulfur, respectively. When the double bond is not present, the compound is a monocyclic pyridine ether or thioether, again depending upon whether $X_3$ is oxygen or sulfur. $X_4$ is —CH$_2R_{21}$ or —CR$_{21}$=, where $R_{21}$ is selected from the group consisting of aryl, heteroaryl, aralkyl, heteroaralkyl, alkylcarbonyl, arylcarbonyl, heteroalkylcarbonyl, heteroaralkylcarbonyl, aralkylcarbonyl, aminocarbonyl, alkylaminocarbonyl, arylaminocarbonyl, dialkylaminocarbonyl, diarylaminocarbonyl, arylalkylaminocarbonyl, carboxyl, alkoxycarbonyl, aryloxycarbonyl, sulfo, alkylsulfonyl and arylsulfonyl; and $X_5$ is hydrogen, alkyl, hydroxyl, alkoxyl, aryloxyl, halogen, cyano, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, carboxyl, alkoxycarbonyl, aryloxycarbonyl, sulfo, alkylsulfonyl, arylsulfonyl or —CR$_{22}$=where $R_{22}$ is selected from the group consisting of hydrogen, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, hydroxyl, halogen, cyano, carboxyl, alkoxycarbonyl and aryloxycarbonyl. When $X_4$ is —CR$_{21}$=, $X_5$ is —CR$_{22}$=, and $X_4$ and $X_5$ are joined by the above-mentioned double bond, to form thereby a fused, bicyclic pyrido[b]thiophene ($X_3$ is sulfur) or pyrido[b]furan ($X_3$ is oxygen) ring system. When $X_4$ is —CH$_2R_{21}$, $X_5$ is not —CR$_{22}$=, thereby forming a pyridine ether ($X_3$ is oxygen) or thioether ($X_3$ is sulfur). $R_{18}$ and $R_{19}$ are selected independently from the group consisting of hydrogen, halogen, hydroxy, aryloxy, alkoxy, lower alkyl, aryl, heteroaryl, aralkyl and heteroaralkyl. $R_{20}$ is selected from the group consisting of alkoxymethyl, dialkoxymethyl, arylalkylaminomethyl, arylaminomethyl, alkylaminomethyl, aminomethyl, diarylaminomethyl, dialkylaminomethyl, hydroximinyl, iminyl, aldehyde, alkylcarbonyl, arylcarbonyl, alkyliminyl, aryliminyl, aralkyliminyl, alkoximinyl, aryloximinyl, heterocycleiminyl, alkoxycarbonyl, aryloxycarbonyl, carboxyl, alkene, —HC=NNHR$_{23}$ where $R_{23}$ is selected from the group consisting of hydrogen, alkyl, aryl, aralkyl, heterocycle, heterocyclealkyl, and —C($X_6$)NHR$_{24}$ where $X_6$ is oxygen or sulfur and $R_{24}$ is selected from the group consisting of hydrogen, aryl, arylsulfonyl, aralkyl, heterocycle and heterocyclealkyl.

One group of preferred compounds of this class include pyrido[b]thiophenes in which $X_3$ is sulfur, $X_4$ is —C(C(O)aryl)= and $X_5$ is —C(NH$_2$)=, especially those pyrido[b]thiophene compounds in which $X_4$ is —C(C(O)p-halophenyl)=.

Another group of compounds of this class includes monocyclic pyridine ethers and thioethers having the following structure ($X_4$ is —CH$_2R_{21}$):

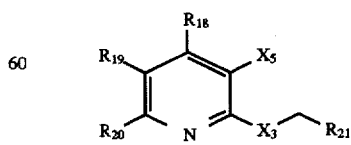

In preferred compounds of the invention having this structure, $X_3$ is oxygen or sulfur; $R_{21}$ is selected from the group consisting of aryl, heteroaryl, aralkyl and heteroaralkyl; $X_5$ is hydrogen or cyano; $R_{18}$ and $R_{19}$ are selected independently from the group consisting of hydrogen, halogen, hydroxyl, lower alkyl, aryl, heteroaryl, aralkyl, alkoxy, aryloxy and heteroaralkyl; and $R_{20}$ is selected from the group consisting of alkoxymethyl, dialkoxymethyl, arylalkylaminomethyl, arylaminomethyl, alkylaminomethyl, aminomethyl, diarylaminomethyl, dialkylaminomethyl, hydroximinyl, iminyl, aldehyde, alkylcarbonyl, arylcarbonyl, alkyliminyl, aryliminyl, aralkyliminyl, alkoximinyl, aryloximinyl, heterocycleiminyl, alkoxycarbonyl, aryloxycarbonyl, carboxyl, alkene, —HC═NNHR$_{23}$ where $R_{23}$ is selected from the group consisting of hydrogen, alkyl, aryl, aralkyl, heterocycle, heterocyclealkyl, and —C($X_6$)NHR$_{24}$ where $X_6$ is oxygen or sulfur and $R_{24}$ is selected from the group consisting of hydrogen, aryl, arylsulfonyl, aralkyl, heterocycle and heterocyclealkyl.

Preferred pyridine thioethers include those in which $X_3$ is sulfur, $X_5$ is cyano and $R_{20}$ is —HC═NNHR$_{23}$, where $R_{23}$ is alkyl or heterocycle.

Yet other preferred pyridine thioether compounds of this invention have structures in which $R_{20}$ is dimethoxymethyl or —CH═NNH—C(S)NH(aryl) and $X_5$ is cyano.

Another group of preferred pyridine thioethers includes compounds in which $X_3$ is sulfur, $R_{21}$ is aryl, $X_5$ is cyano, and $R_{20}$ is aryliminyl, as shown below:

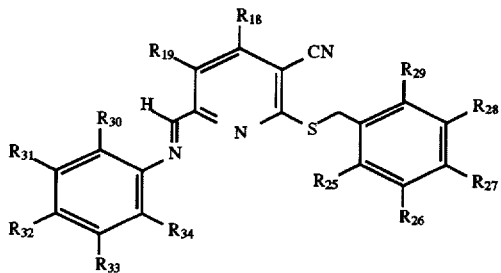

In such compounds, $R_{18}$ and $R_{19}$ are as specified for the immediately preceding structure, and $R_{25}$–$R_{34}$ are preferably selected independently from the group consisting of hydrogen, halogen, lower alkyl, alkoxyl, nitro, cyano, alkylamino and dialkylamino. Further, $R_{31}$ and $R_{32}$ together may be points of attachment for the groups —C(O)—NR$_{35}$C—(O)— and —O—(CH$_2$)$_n$—O— where n is 1 or 2 and $R_{35}$ is hydrogen, aryl, aralkyl or alkyl.

Another preferred group of pyridine thioether compounds of the invention has the following structure:

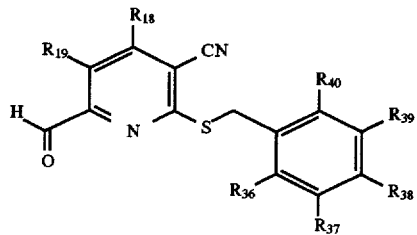

Again, $R_{18}$ and $R_{19}$ are as defined above. In addition, $R_{36}$–$R_{40}$ are selected independently from the group consisting of hydrogen, halogen, alkoxyl, hydroxyl, amino, alkylamino, dialkylamino, arylamino, diarylamino, arylalkylamino, cyano, carboxyl, alkoxycarbonyl, aryloxycarbonyl, aldehyde, arylcarbonyl, alkylcarbonyl, nitro and lower alkyl. Preferred compounds include those in which $R_{36}$–$R_{40}$ are selected independently from the group consisting of hydrogen, halogen and alkyl.

Still other preferred pyridine thioether compounds of this invention have structures in which $R_{20}$ is —CH═NNH (aryl) and $X_5$ is cyano, as shown below:

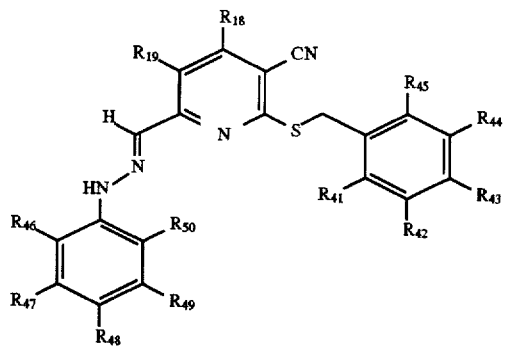

In this structure, $R_{18}$ and $R_{19}$ again are as defined above and $R_{41}$–$R_{50}$ are selected independently from the group consisting of hydrogen, halogen, hydroxyl, amino, alkylamino, arylamino, dialkylamino, diarylamino, arylalkylamino, lower alkyl, alkoxyl, nitro and cyano.

The above benzo[b]thiophene, pyrido[b]thiophene, pyrido[b]furan, pyridine ether and pyridine thioether derivatives have many valuable uses as inhibitors of deleterious telomerase activity, most importantly, the use to treat cancer in humans. The pharmaceutical compositions of this invention can be employed in treatment regimens in which cancer cells are killed, in vivo, as demonstrated by the use of telomerase inhibitors of the invention to kill cancer cells ex vivo. Thus, this invention provides therapeutic compositions for treating cancer, and methods for treating cancer in humans and other mammals (e.g., cows, horses, sheep, steer, pigs and animals of veterinary interest such as cats and dogs).

These and other features of the invention will be described in detail below with reference to the associated structures and tables.

DESCRIPTION OF SPECIFIC EMBODIMENTS

I. Definitions

The term "alkyl" as used herein refers to a straight, branched or cyclic hydrocarbon chain fragment or radical containing between about one and about twenty carbon atoms, more preferably between about one and about ten carbon atoms (e.g., methyl, ethyl, n-propyl, isopropyl, cyclopropyl, n-butyl, iso-butyl, tert-butyl, cyclobutyl, adamantyl, noradamantyl and the like). Straight, branched or cyclic hydrocarbon chains having eight or fewer carbon atoms will also be referred to herein as "lower alkyl". The hydrocarbon chains may further include one or more degrees of unsaturation i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

In addition, the term "alkyl" as used herein further includes one or more substitutions at one or more carbon atoms of the hydrocarbon fragment or radical. Such substitutions include, but are not limited to: aryl; heterocycle; halogen; nitro (—NO$_2$); cyano (—CN); hydroxyl (also referred to herein as "hydroxy"), alkoxyl (also referred herein as alkoxy) or aryloxyl (also referred to herein as "aryloxy", —OR); thio or mercapto, or alkyl or arylthioether (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); aldehyde, or aryl- or alkylcarbonyl (RC(O)—); iminyl, or aryl- or alkyliminyl (—C(=NR)—); sulfo (—SO$_2$OR); or alkyl- or arylsulfonyl (—SO$_2$R); or hydroximinyl, or aryl- or alkoximinyl (—C(=NOR)—); where R and R' independently are hydrogen, aryl or alkyl as defined herein.

The term "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as, but not limited to, sulfonyl (—SO$_2$—), phosphonyl (—PO$_2$—) and methylene (—C(CH$_2$)—). Other carbonyl equivalents will be familiar to those having skill in the medicinal and organic chemical arts.

The term "aryl" as used herein refers to cyclic aromatic carbon chains having twenty or fewer carbon atoms, e.g., phenyl, naphthyl, biphenyl and anthracenyl. One or more carbon atoms may also be substituted with, e.g.: aryl; heterocycle; halogen; nitro (—NO$_2$); cyano (—CN); hydroxyl (also referred to herein as "hydroxy"), alkoxyl (also referred herein as alkoxy) or aryloxyl (also referred to herein as "aryloxy", —OR); thio or mercapto, or alkyl or arylthioether (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); aldehyde, or aryl- or alkylcarbonyl (RC(O)—); iminyl, or aryl- or alkylimnyl (—C(=NR)—); sulfo (—SO$_2$OR); or alkyl- or arylsulfonyl (—SO$_2$R); or hydroximinyl, or aryl- or alkoximinyl (—C(=NOR)—); where R and R' independently are hydrogen, aryl or alkyl as defined herein.

The term "aralkyl" as used herein refers to an aryl group that is joined to a structure by one or more alkyl groups, e.g., benzyl, α-methylbenzyl, phenethyl, and the like .

The term "heterocycle" as used herein refers to a cyclic alkyl group or aryl group as defined above in which one or more carbon atoms of a cyclic alkyl group has been replaced by a non-carbon atom, especially nitrogen, oxygen or sulfur. Aromatic heterocycles are also referred to herein as "heteroaryl". For example, such groups include, but are not limtited to, furyl, tetrahydrofuryl, pyrrolyl, pyrrolidinyl, thienyl, tetrahydrothienyl, oxazolyl, isoxazolyl, triazolyl, thiazolyl, isothiazolym, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimdinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridinyl, phenazinyl, phenothiazinyl, phenoxazinyl, purinyl, benzimidazolyl and benzthiazolyl.

The above heterocyclic groups may further include one or more substituents at one or more carbon and/or non-carbon atoms of the heteroaryl group, e.g.: aryl; heterocycle; halogen; nitro (—NO$_2$); cyano (—CN); hydroxyl (also referred to herein as "hydroxy"), alkoxyl (also referred herein as alkoxy) or aryloxyl (also referred to herein as "aryloxy", —OR); thio or mercapto, or alkyl or arylthioether (—SR); amino, alkylamino, arylamino, dialkyl- or diarylamino, or arylalkylamino (—NRR'); aminocarbonyl, alkylaminocarbonyl, arylaminocarbonyl, dialkylaminocarbonyl, diarylaminocarbonyl or arylalkylaminocarbonyl (—C(O)NRR'); carboxyl, or alkyl- or aryloxycarbonyl (—C(O)OR); aldehyde, or aryl- or alkylcarbonyl (RC(O)—); iminyl, or aryl- or alkyliminyl (—C(=NR)—); sulfo (—SO$_2$OR); or alkyl- or arylsulfonyl (—SO$_2$R); or hydroximinyl, or aryl- or alkoximinyl (—C(=NOR)—); where R and R' independently are hydrogen, aryl or alkyl as defined herein.

The term "heteroaralkyl" as used herein refers to a heteroaryl group that is joined to a parent structure by one or more alkyl groups, e.g., 2-thienylmethyl, and the like.

II. Telomerase Inhibitors

As noted above, the immortalization of cells involves inter alia the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim, et al., incorporated herein by reference above). This analysis, supplemented by data that indicates that the shortening of telomere length can provide the signal for replicative senescence in normal cells, see PCT Application No. 93/23572 (incorporated herein by reference above), demonstrates that inhibition of telomerase activity can be an effective anti-cancer therapy. Thus, telomerase activity can prevent the onset of otherwise normal replicative senescence by preventing the normal reduction of telomere length and the concurrent cessation of cell replication that occurs in normal somatic cells after many cell divisions. In cancer cells, where the malignant phenotype is due to loss of cell cycle or growth controls or other genetic damage, an absence of telomerase activity permits the loss of telomeric DNA during cell division, resulting in chromosomal rearrangements and aberrations that lead ultimately to cell death. However, in cancer cells having telomerase activity, telomeric DNA is not lost during cell division, thereby allowing the cancer cells to become immortal, leading to a terminal prognosis for the patient. Agents capable of inhibiting telomerase activity in tumor cells offer therapeutic benefits with respect to a wide variety of cancers and other conditions (e.g., fungal infections) in which immortalized cells having telomerase activity are a factor in disease progression or in which inhibition of telomerase activity is desired for treatment purposes. The telomerase inhibitors of the invention can also be used to inhibit telomerase activity in germ line cells, which may be useful for contraceptive purposes.

Thus, in one aspect, the present invention provides compounds that can serve as an important weapons against many types of malignancies in the war against cancer. In particular, the compounds of the present invention can provide a highly general method of treating many—if not most—malignancies, as demonstrated by the highly varied human tumor cell lines and tumors having telomerase activity. More importantly, the compounds of the present invention can be effective in providing treatments that discriminate between malignant and normal cells to a high degree, avoiding many of the deleterious side-effects present with most current chemotherapeutic regimes which rely on agents that kill dividing cells indiscriminately.

In one aspect, the present invention provides pharmaceutical compositions and methods relating to compounds having the general structure shown as Compound I below:

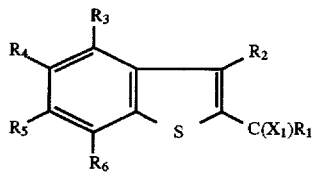

Compound I

In Compound I, $R_1$ is selected from the group consisting of —$OR_7$, —$NR_8R_9$, —$NHNR_{10}R_{11}$, —$NHNHC(X_2)NHR_{12}$, —$NHSO_2NR_8R_9$, —$NHNHC(O)R_{12}$, —$NHNHSO_2R_{12}$ and —$NHC(O)NR_8R_9$, where $R_7$–$R_{12}$ are selected independently from the group consisting of hydrogen, alkyl, aryl, aralkyl, heteroaryl and heteroaralkyl. $X_1$ and $X_2$ are selected independently from the group consisting of oxygen and sulfur. Further, in the above structure, $R_2$ is hydrogen or halogen, and $R_3$–$R_6$ are selected independently from the group consisting of hydrogen, halogen, hydroxyl, —$NR_8R_9$, nitro, cyano, alkoxyl, lower alkyl, aryl and aryloxyl.

Certain of the benzo[b]thiophene compounds of this invention include novel compounds in which either or both $R_2$ or $R_6$ is halogen when $R_7$ is hydrogen, with the limitation that (i) $R_2$ is not chloro when: $R_3$, $R_4$ and $R_6$ are hydrogen, and $R_5$ is chloro, fluoro or hydrogen; or when $R_3$ and $R_4$ are hydrogen, $R_5$ is methoxy and $R_6$ is chloro; or when $R_3$, $R_5$ and $R_6$ are hydrogen and $R_4$ is fluoro; or when $R_3$ is chloro and $R_4$–$R_6$ are hydrogen; (ii) $R_2$ is not bromo when $R_3$–$R_6$ are hydrogen, or when $R_3$–$R_5$ are hydrogen and $R_6$ is methyl, or when $R_3$, $R_5$ and $R_6$ are hydrogen and $R_4$ is methyl, chloro or methoxy, or when $R_3$ is chloro and $R_4$–$R_6$ are hydrogen; and (iii) $R_6$ is not chloro when $R_2$–$R_5$ are hydrogen.

Other novel compounds include those in which, when $R_1$ is —$NHNR_{10}R_{11}$, $R_{11}$ is not tert-butyl, unsubstituted phenyl, hydrogen, 2-thienylmethyl, 2-furanylmethyl, unsubstituted benzyl or α-methylbenzyl, or benzyl or α-methylbenzyl substituted with bromo, chloro, methoxy, methyl, dimethylamino, hydroxyl at the para position of the phenyl ring or substituted with —$NH_2$ or hydroxyl at the ortho position of the phenyl ring, when $R_{10}$ is hydrogen, $R_2$ is chloro and $R_3$–$R_6$ are hydrogen. In addition, when $R_1$ is —$NHNR_{10}R_{11}$, $R_{11}$ is not hydrogen when $R_2$ is chloro, $R_3$, $R_4$, $R_6$ and $R_{10}$ are hydrogen and $R_5$ is methoxy. Furthermore, $R_{11}$ is not tert-butyl when $R_2$, $R_3$, $R_5$, $R_6$ and $R_{10}$ are hydrogen and $R_4$ is fluoro, chloro, trifluoromethyl or hydrogen; or when $R_2$–$R_4$, $R_6$ and $R_{10}$ are hydrogen and $R_5$ is fluoro, chloro, methyl or trifluoromethyl; or when $R_4$ and $R_5$ are both methoxy, fluoro or chloro.

Still other novel compounds include those in which, when $R_1$ is —$NHNHC(O)NHR_{12}$, $R_{12}$ is not methyl, phenyl or phenyl substituted at the para position with methoxy or chloro when $R_2$ is chloro, $R_3$, $R_4$ and $R_6$ are hydrogen and $R_5$ is methoxy or hydrogen. In addition, when $R_5$ is hydrogen, $R_{12}$ also is not para-methylphenyl, unsubstituted benzyl or unsubstituted allyl.

In preferred embodiments, $R_2$ and $R_6$ are selected independently from the group consisting of hydrogen and halogen. Preferably at least one or both of $R_2$ and $R_6$ is halogen, especially chloro. In one preferred embodiment of Compound I, $X_1$ is oxygen and $R_1$ is —$OR_7$. In another preferred embodiment, $X_1$ is oxygen, $R_1$ is —$OR_7$ and $R_7$ is hydrogen or methyl. Also preferred are compounds in which $X_1$ is oxygen, $R_1$ is —OH, —$OCH_3$ or —$NHNH_2$ and $R_5$ is lower alkyl, or alkoxyl. Other preferred embodiments of Compound I are those in which $X_1$ is oxygen, $R_1$ is hydroxyl or methoxy, $R_2$ and $R_6$ are hydrogen or chloro, $R_3$, and $R_4$ are hydrogen, and $R_5$ is methyl or methoxy. Some preferred compounds are shown below (Compounds II–IV).

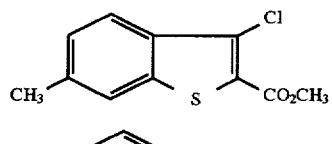

Compound II

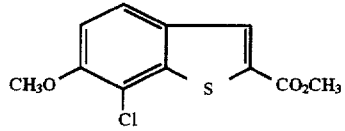

Compound III

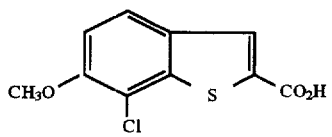

Compound IV

Also preferred are compounds of the general formula shown in Compound I in which $R_1$ is —$NHNHC(X_2)NHR_{12}$, where $X_1$ and $X_2$ are defined as above with respect to Compound I, $R_2$ is hydrogen or chloro, and $R_{12}$ is aryl. These compounds have the structure shown below as Compound V:

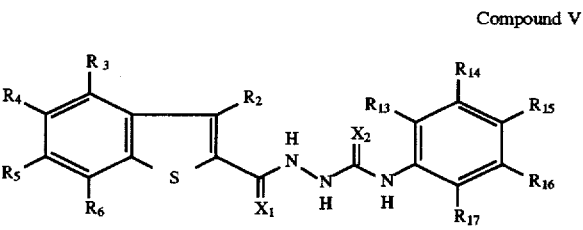

Compound V

In Compound V, $R_{13}$–$R_{17}$ are selected independently from the group consisting of hydrogen, halogen, alkoxyl, lower alkyl, aryl and aryloxyl. As noted above, novel compounds include those in which $R_{15}$ is not methoxy or chloro when $R_2$ is chloro, $R_3$, $R_4$, $R_6$, $R_{13}$, $R_{14}$, $R_{16}$ and $R_{17}$ are hydrogen and $R_5$ is methoxy or hydrogen. Also, when $R_2$ is chloro, $R_3$–$R_6$, $R_{13}$, $R_{14}$, $R_{16}$ and $R_{17}$ are hydrogen, $R_{15}$ also is not methyl.

Preferred embodiments of Compound V include those in which $X_1$ is oxygen and $X_2$ is sulfur. Also preferred are those embodiments in which $X_1$ is oxygen, $X_2$ is sulfur and $R_3$–$R_6$ and $R_{13}$–$R_{17}$ are selected independently from the group consisting of hydrogen, halogen, hydroxyl, nitro, cyano, amino, alkylamino, arylamino, dialkylamino, diarylamino, arylalkylamino, alkoxyl, alkyl, aryl and aryloxyl. Several preferred embodiments of Compound V, in which $X_1$ is oxygen, $X_2$ is sulfur, $R_2$ is chloro, $R_3$–$R_6$ are hydrogen and $R_{13}$–$R_{17}$ are hydrogen or chloro independently, are shown in Table 1 below (Compounds VI–X).

TABLE 1

| Compound | $R_{13}$ | $R_{14}$ | $R_{15}$ | $R_{16}$ | $R_{17}$ |
|---|---|---|---|---|---|
| VI | H | Cl | H | H | Cl |
| VII | H | H | Cl | Cl | H |
| VIII | H | H | Cl | Cl | Cl |
| IX | H | Cl | Cl | H | Cl |
| X | H | H | Cl | H | Cl |

In another embodiment, the present invention provides telomerase inhibiting compounds having the structure shown as Compound XI, in addition to related pharmaceutical compositions and therapeutic methods and uses.

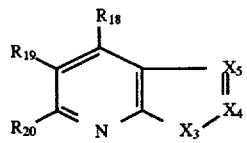

Compound XI

In Compound XI, $X_3$ is oxygen or sulfur; and the double dashed lines indicate an optional double bond, which, when present, forms a fused, bicyclic pyrido[b]furan or pyrido[b]thiophene ring system, depending upon whether $X_3$ is oxygen or sulfur, respectively. When the double bond is not present, Compound XI is either a pyridine ether or thioether, again depending upon whether $X_3$ is oxygen or sulfur. $X_4$ is —$CH_2R_{21}$ or —$CR_{21}$—, where $R_{21}$ is selected from the group consisting of aryl, heteroaryl, aralkyl, heteroaralkyl, alkylcarbonyl, arylcarbonyl, heteroalkylcarbonyl, heteroaralkylcarbonyl, aralkylcarbonyl, aminocarbonyl, alkylaminocarbonyl, arylaminocarbonyl, dialkylaminocarbonyl, diarylaminocarbonyl, arylalkylaminocarbonyl, carboxyl, alkoxycarbonyl, aryloxycarbonyl, sulfo, alkylsulfonyl and arylsulfonyl. $X_5$ is hydrogen, alkyl, hydroxyl, alkoxyl, aryloxyl, halogen, cyano, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, carboxyl, alkoxycarbonyl, aryloxycarbonyl, sulfo, alkylsulfonyl, arylsulfonyl or —$CR_{22}$— where $R_{22}$ is selected from the group consisting of hydrogen, amino, alkylamino, arylamino, dialkylamino, diarylamino, arylalkylamino, aminocarbonyl, alkylaminocarbonyl, arylaminocarbonyl, dialkylaminocarbonyl, diarylaminocarbonyl, arylalkylaminocarbonyl, halogen, cyano, carboxyl, alkoxycarbonyl and aryloxycarbonyl. When $X_4$ is —$CR_{21}$—, $X_5$ is —$CR_{22}$—, and $X_4$ and $X_5$ are joined by the above-mentioned double bond, to form thereby a fused, bicyclic pyrido[b]thiophene ($X_3$ is sulfur) or pyrido[b]furan ($X_3$ is oxygen) ring system. When $X_4$ is —$CH_2R_{21}$, $X_5$ is not —$CR_{22}$—, thereby forming a pyridine ether ($X_3$ is oxygen) or thioether ($X_3$ is sulfur).

In Compound XI above, $R_{18}$ and $R_{19}$ are selected independently from the group consisting of hydrogen, halogen, hydroxy, aryloxy, alkoxy, lower alkyl, aryl, heteroaryl, aralkyl and heteroaralkyl. $R_{20}$ is selected from the group consisting of alkoxymethyl, dialkoxymethyl, arylalkylaminomethyl, arylaminomethyl, alkylaminomethyl, aminomethyl, diarylaminomethyl, dialkylaminomethyl, hydroximinyl, iminyl, aldehyde, alkylcarbonyl, arylcarbonyl, alkyliminyl, aryliminyl, aralkyliminyl, alkoximinyl, aryloximinyl, heterocycleiminyl, alkoxycarbonyl, aryloxycarbonyl, carboxyl, alkene, —HC=$NNHR_{23}$ where $R_{23}$ is selected from the group consisting of hydrogen, alkyl, aryl, aralkyl, heterocycle, heterocyclealkyl, and —$C(X_6)NHR_{24}$ where $X_6$ is oxygen or sulfur and $R_{24}$ is selected from the group consisting of hydrogen, aryl, arylsulfonyl, aralkyl, heterocycle and heterocyclealkyl.

Preferred telomerase inhibiting compounds having the formula shown in Compound XI include those in which $X_3$ is sulfur, $R_{20}$ is —HC=NNH(p-methylphenyl), $X_4$ is —$CR_{21}$—, $X_5$ is —$CR_{22}$— and $X_4$ and $X_5$ are joined by a double bond to form a pyrido[b]thiophene ring system. Also preferred are those compounds in which $R_{21}$ is phenylcarbonyl and $R_{22}$ is amino. Also preferred are those compounds in which $R_{21}$ is para-bromophenylcarbonyl or para-fluorophenylcarbonyl and $R_{22}$ is amino, as shown below (Compounds XII and XIII). Although only one stereoisomer for each of Compound XII and XIII is shown, any structure shown herein having more than one possible stereoisomer will be assumed to represent also each possible stereoisomer in pure form, in addition to a mixture of stereoisomers unless otherwise indicated. Methods for isolating and/or synthesizing pure stereoisomers can be performed using well known methods and materials.

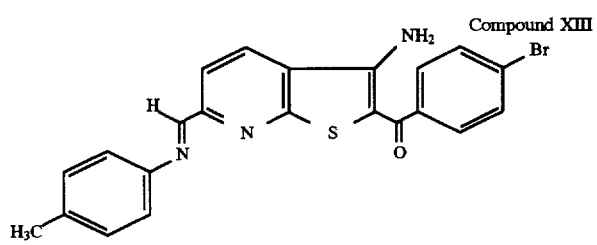

Compound XII

Compound XIII

Another preferred class of compounds related to Compound XI is that in which $X_4$ is —$CH_2R_{21}$ and $X_5$ is cyano, aminocarbonyl, alkylaminocarbonyl, arylaminocarbonyl, dialkylaminocarbonyl or arylalkylaminocarbonyl, alkoxycarbonyl, aryloxycarbonyl or carboxyl, i.e., pyridine ethers and thioethers. This class is illustrated generally by Compound XIV below.

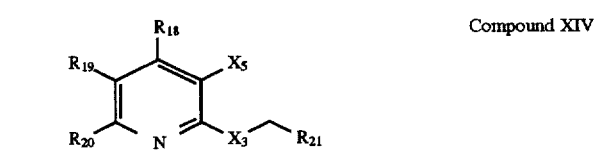

Compound XIV

Preferred embodiments of Compound XIV are those in which $X_3$ is sulfur and $X_5$ is cyano. Also preferred are embodiments in which $X_3$ is sulfur, $X_5$ is cyano and $R_{20}$ is aryliminyl, heterocycleiminyl or alkyliminyl. Also preferred are those embodiments in which $X_3$ is sulfur, $X_5$ is cyano, $R_{20}$ is aryliminyl and $R_{21}$ is aryl or heteroaryl.

Especially preferred are those compounds in which $R_{21}$ is phenyl, as shown by Compound XV below:

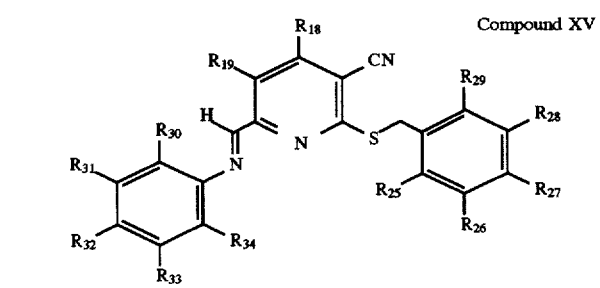

Compound XV

In Compound XV, $R_{25}$–$R_{34}$ are selected independently from the group consisting of hydrogen, halogen, lower alkyl, alkoxyl, nitro, cyano, alkylamino and dialkylamino. Furthermore, $R_{31}$ and $R_{32}$ together may be points of attachment for the groups —C(O)—$NR_{35}$C—(O)— and —O—$(CH_2)_n$—O— where n is 1 or 2 and $R_{35}$ is hydrogen, aryl, aralkyl or alkyl. Preferred compounds having the structure of Compound XV and the just-described substitution pattern are those in which $R_{25}$–$R_{29}$ are selected independently from the group consisting of hydrogen and halogen.

Especially preferred compounds (Compounds XVI–XXVII) of the class defined by Compound XV are those in which $R_{18}$, $R_{19}$, $R_{25}$, $R_{26}$, $R_{29}$, $R_{30}$, $R_{33}$ and $R_{34}$ are hydrogen, and $R_{27}$, $R_{28}$, $R_{31}$ and $R_{32}$ are as shown below in Table 2 below.

which $R_{27}$, $R_{29}$, $R_{31}$ and $R_{32}$ are chloro and $R_{25}$, $R_{26}$, and $R_{28}$ are hydrogen (Compound XXVIII), and compounds in which $R_{31}$ and $R_{32}$ are joined to form cyclic ethers and phthalimide derivatives (Compounds XXIX–XXXI) as shown below:

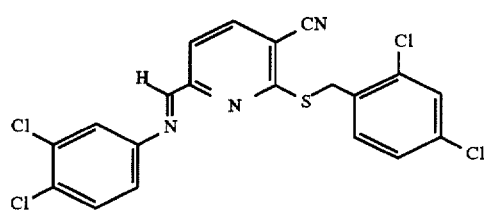
Compound XXVIII

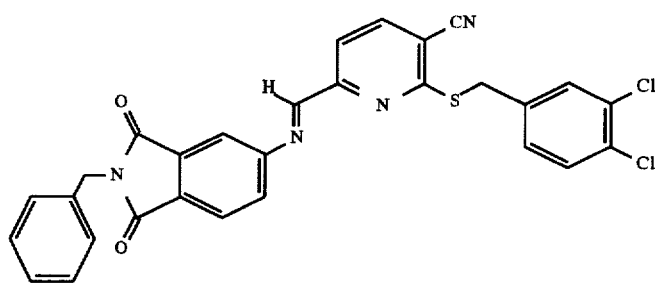
Compound XXIX

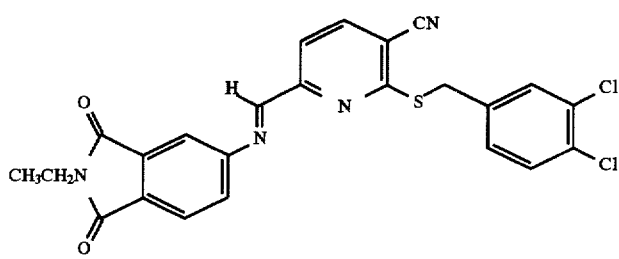
Compound XXX

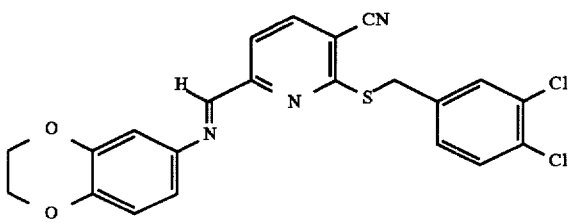
Compound XXXI

TABLE 2

| Compound | $R_{27}$ | $R_{28}$ | $R_{31}$ | $R_{32}$ |
|---|---|---|---|---|
| XVI | Cl | H | H | OCH$_3$ |
| XVII | Cl | H | H | Cl |
| XVIII | Cl | H | H | CH$_3$ |
| XIX | Cl | Cl | H | OCH$_3$ |
| XX | Cl | Cl | H | Cl |
| XXI | Cl | Cl | H | CH$_3$ |
| XXII | Cl | Cl | CF$_3$ | Br |
| XXIII | Cl | Cl | NO$_2$ | Cl |
| XXIV | Cl | Cl | Cl | CN |
| XXV | Cl | Cl | F | F |
| XXVI | Cl | Cl | H | N(CH$_3$)$_2$ |
| XXVII | Cl | Cl | Cl | Cl |

Additional preferred compounds within the class shown generally by Compound XV above include compounds in Still other preferred compounds include those having the generic formula of Compound XV, but in which $X_5$ is cyano, $R_{21}$ is aryl and $R_{20}$ is alkyl- or heterocycleiminyl, and, more preferably, those compounds in which the alkyl substituent of the alkyliminyl group is cyclic alkyl. Also preferred are cyclic alkyl and heterocycle substituents having more than about six constituent atoms, such as Compounds XXXII–XXXVI below.

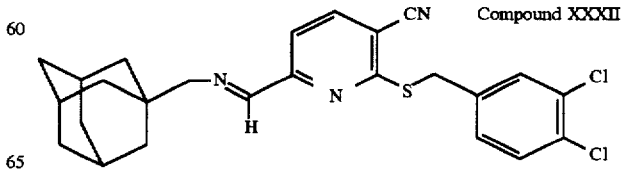
Compound XXXII

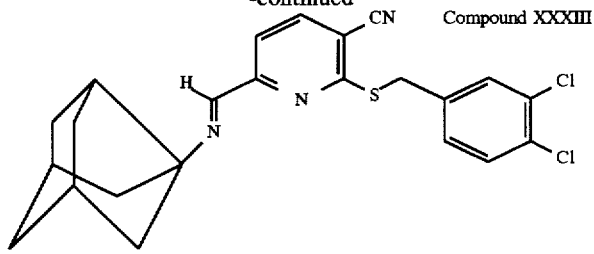
Compound XXXIII

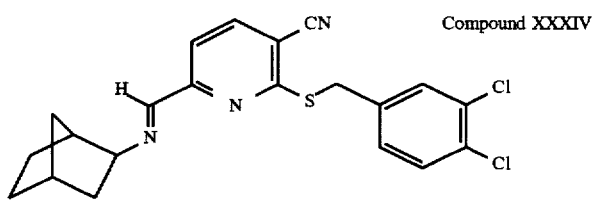
Compound XXXIV

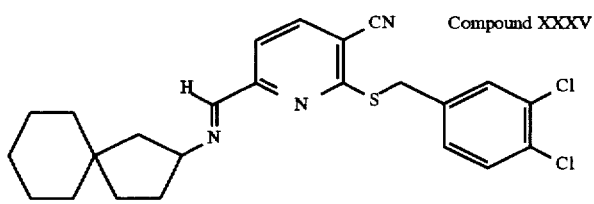
Compound XXXV

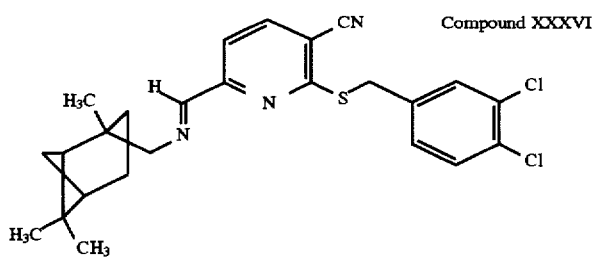
Compound XXXVI

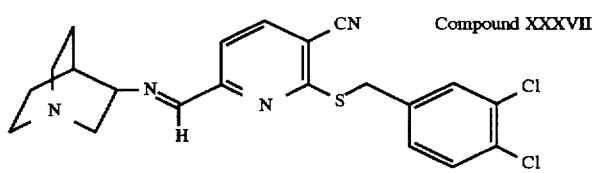
Compound XXXVII

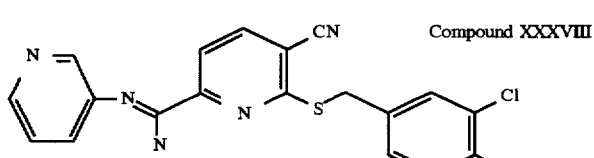
Compound XXXVIII

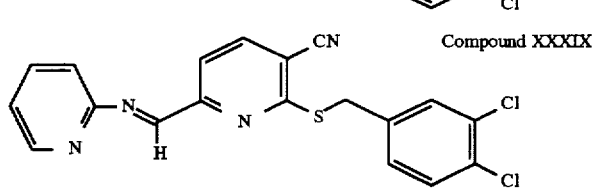
Compound XXXIX

The structure of each of compounds XVI–XXXIX is represented by the structure of Compound XIV, in which $R_{20}$ is aryl-, alkyl- or heterocycleiminyl, $R_{21}$ is phenyl and $X_3$ is sulfur. Other preferred embodiments are those in which $R_{20}$ of Compound XIV above is an aldehyde (—C(O)H). Preferred compounds of this type include those in which $X_5$ is cyano. Also preferred are those in which $X_5$ is cyano and $R_{21}$ is aryl or heteroaryl. Especially preferred compounds have the structure shown for Compound XL below:

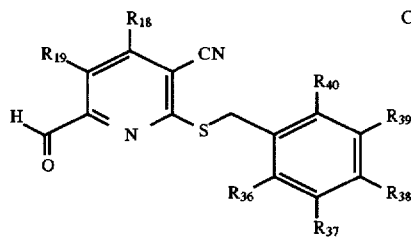
Compound XL

In a preferred embodiment of Compound XL, $R_{36}$–$R_{40}$ are selected independently from the group consisting of hydrogen, halogen, alkoxyl, hydroxyl, amino, alkylamino, dialkylamino, arylamino, diarylamino, arylalkylamino, cyano, carboxyl, alkoxycarbonyl, aryloxycarbonyl, aldehyde, arylcarbonyl, alkylcarbonyl, nitro and lower alkyl. More preferred embodiments of Compound XL are those in which $R_{36}$ $R_{37}$ and $R_{40}$ are hydrogen, $R_{38}$ is chloro and $R_{39}$ is hydrogen or chloro. Compounds XLI and XLII, are shown below:

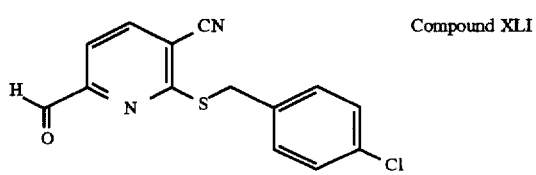
Compound XLI

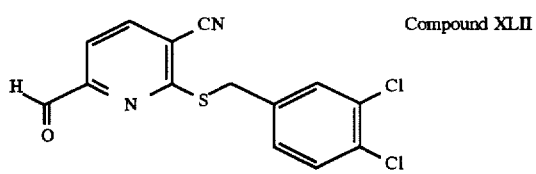
Compound XLII

Other preferred embodiments of Compound XIV are those in which $R_{20}$ is dimethoxymethyl (—CH(OCH$_3$)$_2$), and more preferably, those in which $R_{20}$ is dimethoxymethyl and $X_5$ is cyano.

Another preferred embodiment of Compound XIV includes compounds in which $R_{20}$ is —CH=NNHR$_{23}$, and, especially, those in which $R_{21}$ and $R_{23}$ are aryl and $X_5$ is cyano. A referred structure is shown below (Compound XLIII):

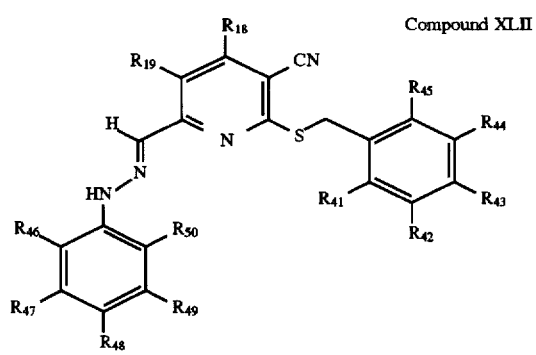
Compound XLII

In Compound XLIII above, $R_{41}$–$R_{50}$ are selected independently from the group consisting of hydrogen, halogen, hydroxyl, amino, alkylamino, arylamino, dialkylamino, diarylamino, arylalkylamino, lower alkyl, alkoxyl, nitro and cyano. In a preferred embodiment of Compound XLIII, $R_{41}$–$R_{50}$ are selected independently from the group consisting of hydrogen and halogen. Especially preferred are Compounds XLIV and XLV below:

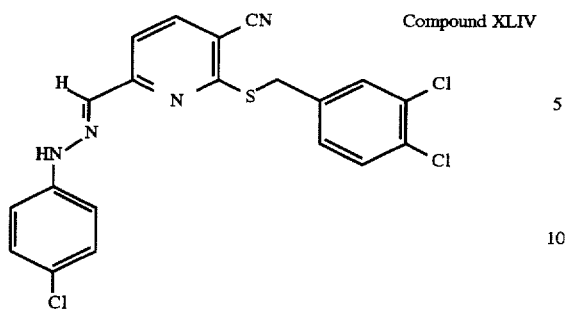

Compound XLIV

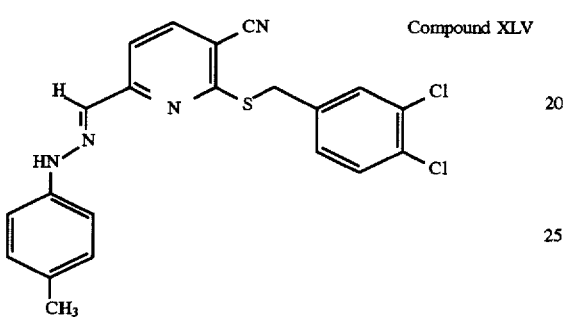

Compound XLV

In still another preferred embodiment of Compound XIV, $R_{20}$ is —HC=NNHR$_{23}$, where $R_{23}$ is —C(S)NHR$_{24}$ as described above. Preferably, $R_{24}$ is aryl. More preferably, $R_{21}$ and $R_{24}$ are aryl and $X_5$ is cyano as shown in Compound XLVI below.

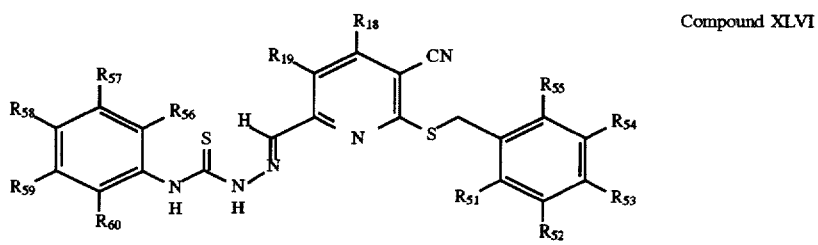

Compound XLVI

In Compound XLVI, $R_{51}$–$R_{55}$ are selected independently from the group consisting of hydrogen, alkyl and halogen, and $R_{56}$–$R_{60}$ are selected independently from the group consisting of alkyl, aryl, heterocycle, halogen, nitro, cyano, hydroxyl, alkoxyl or aryloxyl, amino, alkylamino, arylamino, dialkylamino, diarylamino, arylalkylamino, aminocarbonyl, alkylaminocarbonyl, arylaminocarbonyl, dialkylaminocarbonyl or arylalkylaminocarbonyl, carboxyl, alkoxycarbonyl, aryloxycarbonyl, aldehyde, or arylcarbonyl, alkylcarbonyl, iminyl, aryliminyl, alkyliminyl, sulfo, alkylsulfonyl, arylsulfonyl, hydroximinyl, aryloximinyl and alkoximinyl. More preferred embodiments of Compound XLVI are Compounds XLVII and XLVIII below.

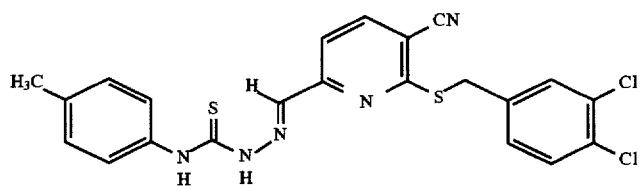

Compound XLVII

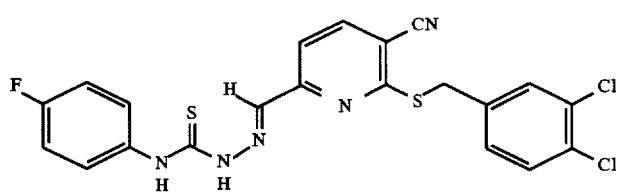

Compound XLVIII

III. Synthesis of Telomerase Inhibitors

The compounds of the present invention can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 3rd Ed., Vols. A and B (Plenum 1992), and Green and Wuts, PROTECTIVE GROUPS IN ORGANIC SYNTHESIS 2nd Ed. (Wiley 1991), each of which is incorporated herein by reference. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

Compounds of the class represented by Compound I can be synthesized using the following general procedure (Scheme 1).

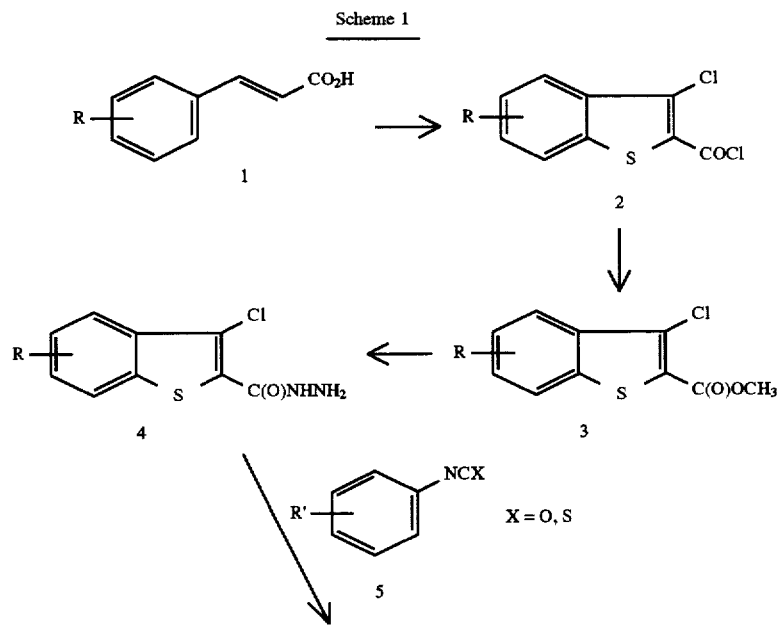

Scheme 1

-continued
Scheme 1

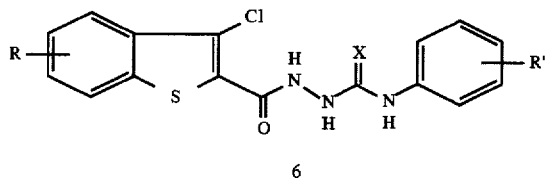

6

Starting from the appropriately substituted cinnamic acid 1, prepared from standard methods and procedures or purchased commercially (e.g., Aldrich), reaction with thionyl chloride under reflux provides the corresponding 3-chlorobenzo[b]thiophene-2-carbonyl chloride 2. Reaction of the acid chloride 2 using, e.g., trimethylsilyl chloride ($Si(CH_3)_3Cl$) and an alcohol (e.g., methanol) provides the corresponding ester 3. Ester 3 corresponds generally to Compounds II–IV above. If the hydrazide is desired, that derivative can be prepared from the ester 3 by reaction with hydrazine in methanol to produce the hydrazide 4. Additional hydrazide derivatives, containing carbonyl or thiocarbonyl substituents on the terminal hydrazide nitrogen, can be prepared, e.g., by reaction of hydrazide 4 with an appropriately substituted isocyanate or isothiocyanate 5 to produce the corresponding addition product 6. This addition product corresponds to Compounds V–X, illustrated above. Examples of each of the transformations outlined above are presented below. The above-described transformations are well known in the art (see, e.g., Reid, W., et al. 1980. *Liebigs. Ann. Chem.* 1424–1427; Connor, D. T., et al. 1992. *J. Med. Chem.* 35(5):958–965; Higa, T., and Krubsack, A. J. 1976. *J. Org. Chem.* 41(21): 3399–3403; and Higa, T., and Krubsack, A. J. 1976. *J. Org. Chem.* 40(21): 3037–3045, each which is incorporated herein by reference.)

Compounds of the class represented by Compound XI can be synthesized using the following general procedure (Scheme 2). The use of the substituent identifiers R, R', R" and R'" is merely to indicate the presence of one or more substituents at the position or moiety indicated. The values of R, R', R" and R'" shown in Scheme 2 below can be determined by reference to the specific moieties described above in connection with the structure of Compound XI.

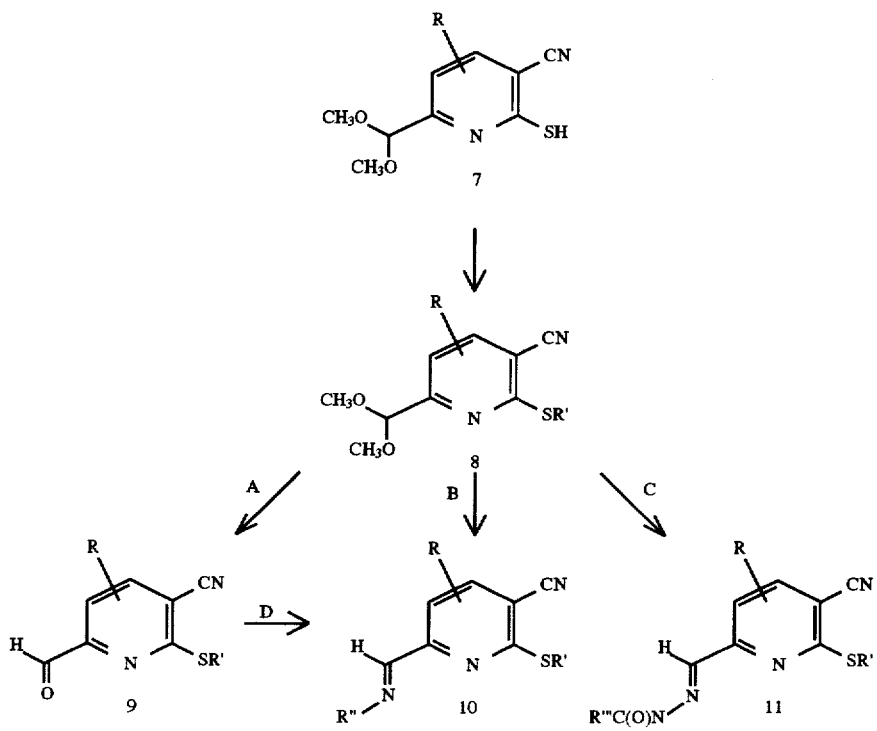

With the appropriately substituted derivative of commercially available 2-thio-3-cyano-5-(dimethoxymethyl) pyridine 7, reaction with an appropriate alkylating agent or other nucleophile under basic conditions (e.g., potassium carbonate ($K_2CO_3$) in dimethylformamide (DMF) followed by addition of R'X, where X is a halide or other suitable leaving group such as tosyl) provides the desired thioether 8. Removal of the acetal group using standard conditions (e.g., p-toluenesulfonic acid in benzene), provides aldehyde 9 (pathway A).

Formation of imine 10 can be accomplished by conversion of the acetal 8 or aldehyde 9 by reaction with an appropriately substituted amine under standard conditions.

e.g., by heating the acetal or aldehyde with the amine in benzene with 3 Å molecular sieves in the presence of an acid (pathways B and D). Similarly, reaction of the acetal 8 with an appropriately substituted hydrazide or semicarbazide and acid (e.g., HCl), provides the desired hydrazide 11 (pathway C). Alternatively, in some cases the imine 10 can be formed directly from the corresponding aldehyde 9 (Pathway D). Additional synthetic routes to compounds 9, 10, and 11 will be apparent to those having skill in the art based on the disclosure herein.

A more specific example of the general synthetic procedure just described above is presented below (Scheme 3). Again, R, R' and R" are as defined above.

used herein, the term "in vitro" refers to tests performed using living cells in tissue culture. Such procedures are also known as "ex vivo".

One method used to identify compounds of the invention that inhibit telomerase activity involves placing cells, tissues, or preferably a cellular extract or other preparation containing telomerase in contact with several known concentrations of a test compound in a buffer compatible with telomerase activity. The level of telomerase activity for each concentration of test compound is measured and the $IC_{50}$ (the concentration of the test compound at which the observed activity for a sample preparation was observed to fall one-half of its original or a control value) for the

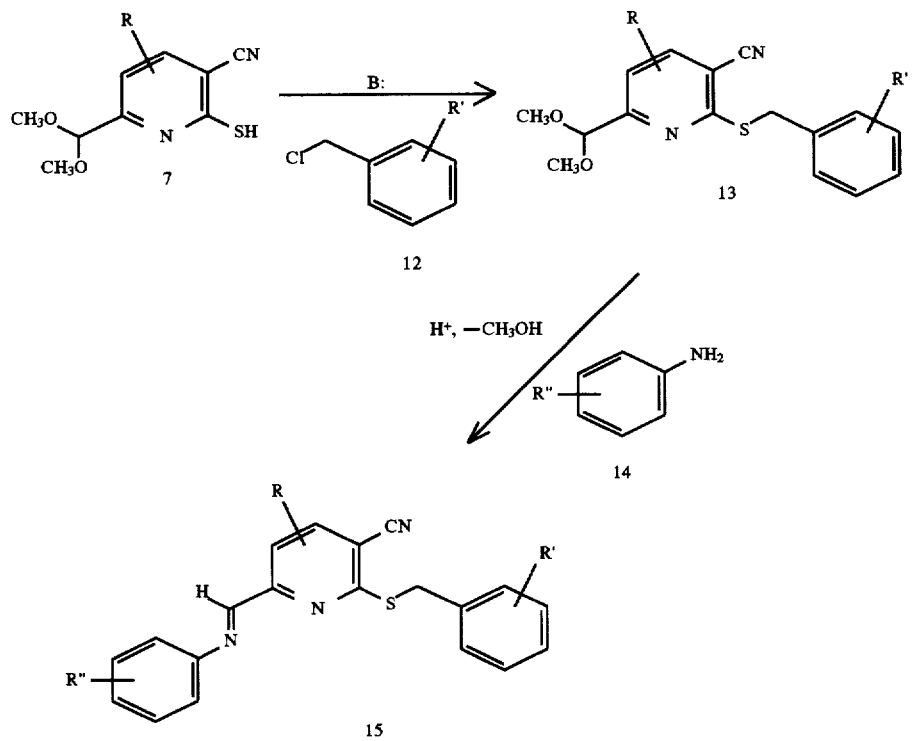

Scheme 3

Starting from commercially available 2-thio-3-cyano-5-(dimethoxymethyl)pyridine 7 (Ryan Scientific), removal of the thiol proton using base (B:, e.g., $K_2CO_3$ in DMF) and introduction of the appropriately substituted benzylchloride derivative 12 under substantially anhydrous conditions provides the benzylthioether 13. Removal of the dimethylacetal group under acidic conditions, followed by imine formation with aniline derivative 14 produces the desired arylimine 15. The benzyl chloride and aniline derivatives can be purchased commercially (e.g., Aldrich) or made using standard methods. The reactions to form the thioether 13 and the imine are performed using standard methods.

Protocols from which the individual Compounds II–IV, VI–X, XII, XIII, XVI–XXXIX, XLI, XLII, XLIV, XLV, XLVII and XLVIII above can be synthesized are provided in the Examples below.

IV. Anti-Tumor Activity of the Telomerase Inhibitors of the Invention

The compounds of the present invention demonstrate inhibitory activity against telomerase in vitro and in vivo, as has been and can be demonstrated as described below. As compound is determined using standard techniques. Other methods for determining the inhibitory concentration of a compound of the invention against telomerase can be employed as will be apparent to those of skill in the art based on the disclosure herein.

A particularly preferred version of this method includes the following steps: (1) incubating a compound of the present invention at a known concentration (e.g., 1000 µM, 320 µM, 100 µM, 32 µM, 10 µM, 3.2 µM and 1.0 µM in DMSO) with telomerase in the presence of an oligonucleotide substrate for human telomerase in a reaction mixture comprising deoxyribonucleotide triphosphates and a buffer in which telomerase is active; (2) immobilizing non-chromosomal DNA (either together with, or separated from, chromosomal DNA) from the reaction mixture resulting from step (1) on a solid support; (3) hybridizing to the DNA a labeled oligonucleotide probe complementary to a nucleic acid sequence added to the substrate by telomerase; and (4) measuring an amount of the labeled probe specifically hybridized to the DNA in comparison to a control reaction in which no test compound is present. A detailed description of appropriate materials, conditions, procedures, etc. for carrying out each step of this method is provided in U.S. patent application Ser. No. 08/288,501, filed Aug. 10, 1994 (previously incorporated herein by reference).

With the above-described methods, $IC_{50}$ values for several of the compounds of the present invention were determined. The values reported in Table 3 below are only approximate values; more exact $IC_{50}$ values can be obtained by repetitive testing.

TABLE 3

| Compound | $IC_{50}$ (μM) | Compound | $IC_{50}$ (μM) |
|---|---|---|---|
| II | 7 | XXVI | 29 |
| III | 2 | XXVII | 29 |
| IV | 3 | XXVIII | 29 |
| VI | 24 | XXIX | 10 |
| VII | 12 | XXX | 10 |
| VIII | 11 | XXXI | 13 |
| IX | 12 | XXXII | 15 |
| X | 15 | XXXIII | 15 |
| XII | 20 | XXXIV | 8 |
| XIII | 20 | XXXVI | 18 |
| XVI | 29 | XXXVII | 4 |
| XVII | 29 | XXXVIII | 16 |
| XVIII | 29 | XXXIX | 13 |
| XIX | 7 | XLI | 10 |
| XX | 12 | XLII | 6 |
| XXI | 9 | XLIV | 19 |
| XXII | 10 | XLV | 19 |
| XXIII | 20 | XLVII | 18 |
| XXIV | 13 | XLVIII | 18 |
| XXV | 13 | | |

As shown in Table I, all of the compounds have anti-telomerase activity (i.e., $IC_{50}$<50 μM). Several of the compounds of the invention (II–IV, VII–X, XIX–XXII, XXIV, XXV, XXIX–XXXIV, XXXIX, XLI, and XLII) are potent telomerase inhibitors, having approximate $IC_{50}$ values of less than about 15 μM.

Compounds of the invention also demonstrate anti-telomerase activity in vitro. In one example, Compound XVIII was found to induce crisis in human immortal embryonic kidney cells in which telomerase activity was present. At a concentration of 3.2 μM, this compound induced crisis in HEK-293 cells within 16 weeks, and caused a reduction of telomere length by about 330 base pairs (bp). At a concentration of 10 μM, crisis was induced within 12 weeks and caused a 350 bp reduction in telomere length.

In another example, Compound XVIII induced telomere reduction during cell division in human ovarian tumor cell lines (OVCAR-5 and SK-OV-3) at a concentration of 10 μM. Importantly, however, in normal BJ cells of fibroblast origin (used as a control), the observed reduction in telomere length was found to be no different from cells treated with a dimethyl sulfoxide (DMSO) control. Compound XVIII also demonstrated no significant cytotoxic effects at a concentration below about 15 μM in the same cells, although some delay through mitosis was observed by cell cycle analysis at concentrations between 5 μM and 15 μM.

In addition, Compound XVIII was found to be highly specific for telomerase in comparison to other enzymes in vitro, as demonstrated by a comparison of the $IC_{50}$ for Compound XVIII against telomerase, and proteins having similar nucleic acid binding or modifying activity similar to telomerase, including DNA Polymerase I, HeLa RNA Polymerase II, T3 RNA Polymerase, MMLV Reverse Transcriptase, Topoisomerase I, Terminal Transferase and Single-Stranded DNA Binding Protein (SSB). Compound XVIII was also found to be highly specific for telomerase as compared to Glucose-6-Phosphate Dehydrogenase. These tests showed that Compound XVIII was highly specific for telomerase at concentrations effective in in vitro testing.

In vivo testing can also be performed using a mouse xenograft model in which OVCAR-5 tumor cells are grafted onto nude mice. As discussed in Example B. 2 below, mice treated with Compound XVIII are expected to have tumor masses that, on average, may increase for a period following the initial dosing, but will begin to shrink in mass with continuing treatment. In contrast, mice treated with a control (DMSO) are expected to have tumor masses that continue to increase. Compound XVIII of the invention was found to be highly effective in halting the growth of tumor cells in vitro and is expected to be highly effective in vivo.

From the foregoing those skilled in the art will appreciate that the present invention also provides methods for selecting treatment regimens involving administration of a compound of the invention. For such purposes, it may be helpful to perform a TRF analysis in which DNA from tumor cells is analyzed by digestion with restriction enzymes specific for sequences other than the telomeric $(T_2AG_3)_N$ sequence. Following digestion of the DNA, gel electrophoresis is performed to separate the restriction fragments according to size. The separated fragments are then probed with nucleic acid probes specific for telomeric sequences to determine the lengths of the telomeres of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

V. Telomerase Inhibiting Compositions and Methods for Treating Diseases With the Same The present invention also provides pharmaceutical compositions for treating cancer and other conditions in which inhibition of telomerase is an effective therapy. These compositions include a therapeutically effective amount of a telomerase inhibiting compound of the invention in a pharmaceutically acceptable carrier or salt.

In one preferred embodiment, the present invention provides a composition effective for treating cancer in a mammal. The composition includes a therapeutically effective amount of a compound having the structure shown below in a pharmaceutically acceptable carrier:

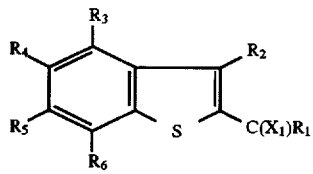

In the structure, $R_1$ is selected from the group consisting of —$OR_7$, —$NR_8R_9$, —$NHNR_{10}R_{11}$, —$NHNHC(X_2)NHR_{12}$, —$NHSO_2NR_8R_9$, —$NHNHC(O)R_{12}$, —$NHNHSO_2R_{12}$ and —$NHC(O)NR_8R_9$, where $R_7$–$R_{12}$ are selected independently from the group consisting of hydrogen, alkyl, aryl, aralkyl, heteroaryl and heteroaralkyl. $X_1$ and $X_2$ are selected independently from the group consisting of oxygen and sulfur. Further, in the above structure, $R_2$ is hydrogen or halogen, and $R_3$–$R_6$ are selected independently from the group consisting of hydrogen, halogen, hydroxyl, —$NR_8R_9$, nitro, cyano, alkoxyl, lower alkyl, aryl and aryloxyl.

In another aspect, the present invention includes a composition for treating cancer in a mammal, comprising a therapeutically effective amount of any of the compounds embraced by the structure of Compound XI in a pharmaceutically acceptable carrier.

In addition, it will be appreciated that therapeutic benefits can be realized by combining a telomerase inhibitor of the invention with other anti-cancer agents (including other inhibitors of telomerase) for treatment of cancer. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g. radiation, surgery, chemotherapy and/or hormonal treatments). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

In one such method, a pharmaceutical formulation comprises a telomerase inhibitor of the invention with an anti-angiogenesis agent, such as fumagillin, fumagillin derivatives, or AGM-1470. The latter compound is available from Takeda Chemical Industries, Ltd., while the former compounds are described in Ingber, et al., Dec. 6, 1990, "Synthetic analogues of fumagillin that inhibit angiogenesis and suppress tumor growth", Nature 348:555–557, incorporated herein by reference for all purposes. Other combinations may include, but are not limited to, a telomerase inhibitor of the invention in addition to one or more antineoplastic agents or adjuncts (e.g., folinic acid or mesna).

Antineoplastic agents suitable for combination with the compounds of the present invention include, but are not limited to, alkylating agents including alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophosphoramide and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine and ranimustine. Additional agents include dacarbazine, mannomustine, mitobronitol, mitolactol and pipobroman. Still other classes of relevant agents include antibiotics, hormonal antineoplastics and antimetabolites. Yet other combinations will be apparent to those of skill in the art.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl inmidodiphosphate, kanamycin, kasugamycin, kirromycin, and O-methyl threonine. Additional protein synthesis inhibitors include modeccin, neomycin, norvaline, pactamycin, paromomycine, puromycin, ricin, ($\alpha$-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide intertwining agents such as distamycin and netropsin, can also be combined with compounds of the present invention in pharmaceutical compositions. DNA base analogs such as acyclovir, adenine $\beta$-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine $\beta$-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine, and RNA synthesis inhibitors including actinomycin D, $\alpha$-amanitine and other fungal amatoxins, cordycepin (3'-deoxyadenosine), dichlororibofuranosyl benzimnidazole, rifampicine and streptovaricin and streptolydigin also can be combined with the compounds of the invention to provide pharmaceutical compositions.

In another embodiment, the present invention includes compounds and compositions in which a telomerase inhibitor is either combined with or covalently bound to a cytotoxic agent bound to a targeting agent, such as a monoclonal antibody (e.g., a murine or humanized monoclonal antibody). It will be appreciated that the latter combination may allow the introduction of cytotoxic agents into cancer cells with greater specificity. Thus, the active form of the cytotoxic agent (i.e., the free form) will be present only in cells targeted by the antibody. Of course, the telomerase inhibitors of the invention may also be combined with monoclonal antibodies that have therapeutic activity against cancer.

In general, a suitable effective dose of a compound of the invention will be in the range of 0.001 to 1000 milligram (mg) per kilogram (kg) of body weight of the recipient per day, preferably in the range of 0.001 to 100 mg per kg of body weight per day, more preferably between about 0.1 and 100 mg per kg of body weight per day and still more preferably in the range of between 0.1 to 10 mg per kg of body weight per day. The desired dosage is preferably presented in one, two, three, four, or more subdoses administered at appropriate intervals throughout the day. These subdoses can be administered as unit dosage form, for example, containing 5 to 10,000 mg, preferably 10 to 1000 mg of active ingredient per unit dosage from. Preferably, the dosage is presented once per day at a dosing at least equal to TID.

The composition used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., REMINGTON'S PHARMACEUTICAL SCIENCES, Mack Publishing Co.: Easton, Pa., 17th Ed. (1985). Preferably, administration will be by oral or parenteral (including subcutaneous, intramuscular, intravenous, and intradermal) routes. More preferably, the route of administration will be oral. The therapeutic methods and agents of this invention can of course be used concomitantly or in combination with other methods and agents for treating a particular disease or disease condition.

While it is possible to administer the active ingredient of this invention alone, it is preferable to present a therapeutic agent as part of a pharmaceutical formulation or composition. The formulations of the present invention comprise at least one telomerase activity-inhibiting compound of this invention in a therapeutically or pharmaceutically effective dose together with one or more pharmaceutically or therapeutically acceptable carriers and optionally other therapeutic ingredients. Various considerations for preparing such formulations are described, e.g., in Gilman et al. (eds.) GOODMAN AND GILMAN'S: THE PHARMACOLOGICAL BASES OF THERAPEUTCS, 8th Ed., Pergamon Press (1990); and REMINGTON'S supra, each of which is incorporated herein by reference for all purposes. Methods for administration are discussed therein, e.g., for oral, intravenous, intraperitoneal, intramuscular, and other forms of administration. Generally, oral administration is preferred.

Typically, methods for administering pharmaceutical compositions will be either topical, parenteral, or oral administration methods for prophylactic and/or therapeutic treatment. Oral administration is a preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013; 4,460,562; 4,466,953; 4,482,534; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases such as skin cancer and fungal infections of the skin (pathogenic fungi typically express telomerase activity).

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a telomerase inhibitor of the invention would be enhanced, one can select a composition for delivery to a mucosal membrane, e.g., in cases of colon cancer one can use a suppository to deliver the telomerase inhibitor.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol, or the like. These compositions will be sterilized by conventional, well known sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolarmine oleate, etc. Such formulations will be useful in treating ovarian cancers.

Another method of parenteral administration employs the implantation of a slow-release or sustained-release system, such that a constant level of dosage is maintained. See, e.g., U.S. Pat. No. 3,710,795, incorporated herein by reference.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art; for example, see REMINGTON'S PHARMACEUTICAL SCIENCES, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds of the invention can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In addition to internal (in vivo) administration, the compounds and compositions of the invention may be applied ex vivo to achieve therapeutic effects, as for example, in the case of a patient suffering from leukemia. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agent for longer periods or at higher concentrations than otherwise available.

Once improvement of the patient's conditions has occurred, as, for example, by the occurrence of remission in the case of a cancer patient, a maintenance dose is administered, if necessary. Subsequently, the dosage or the frequency of administration, or both, can be reduced, as a function of the systems, to a level at which the improved condition is retained. When the symptoms have been alleviated to the desired level, treatment can cease. Patients can, however, require additional treatment upon any recurrence of the disease symptoms.

In prophylactic applications (e.g. chemoprevention), compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

As will be apparent to those of skill in the art upon reading of this disclosure, the present invention provides valuable reagents relating to human telomerase. The above description of necessity provides a limited and merely illustrative sampling of specific compounds, and should not be construed as limiting the scope of the invention. Other features and advantages of the invention will be apparent from the following examples and claims.

EXAMPLES

The following examples describe specific aspects of the invention to illustrate the invention and also provide a description of the methods used to identify and test compounds that inhibit the activity of telomerase to aid those of skill in the art in understanding and practicing the invention. The examples should not be construed as limiting the invention, in any manner.

A. Chemical Syntheses

1. Synthesis of Compounds I–X

The following procedures illustrate the syntheses of compounds in the class defined by the structure of Compound I. Synthesis of 6-Methoxy-3-Chlorobenzo[b]thiophene-2-Carbonyl Chloride A 100 milliliter (ml) 3-necked, round-bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and allowed to cool to room temperature. The reaction flask was then charged with 4-methoxycinnamic acid (Aldrich, 10 g, 60 mmole), anhydrous pyridine (Aldrich, 1 ml, 12.4 mmole), anhydrous dimethylformamide (Aldrich, 2.0 ml, 25.8 mmole) and anhydrous chlorobenzene (Aldrich, 10 ml) at room temperature. At this point the apparatus was disconnected from the dry nitrogen source.

Thionyl chloride (Aldrich, 205.6 mmole, 15 ml) was added to the reaction mixture in a dropwise fashion over a period of 10 minutes using a syringe. Evolution of hydrogen chloride was observed together with the rapid dissolution of the white solid in the flask to give a yellow-brown solution. Upon completion of the addition, the reaction mixture was stirred rapidly at room temperature for 30 minutes and then heated by means of a heating mantle to 140–145 °C. for 5 hours. Upon cooling the reaction mixture to room temperature, the dark brown solution solidified.

The contents of the flask were broken into small pieces, slurried and transferred to a 500 ml Erlenmeyer flask using hot, dry hexane (500 ml, dried over magnesium sulfate, 25 g/1000 ml). The hot hexane slurry was heated to boiling for 30 minutes during which time most of the residue gradually dissolved. The resulting orange-yellow hot hexane solution was decanted from the remaining residue and concentrated to 350 ml. The solution was allowed to cool to room temperature, and was stored at 4° C. overnight. During this period a yellow precipitate formed. The precipitate was filtered off and dried in vacuo to give 4.00 g of the desired material. Further concentration of the filtrate to 200 ml and repeating the above mentioned crystallization steps yielded an additional 1.00 g. $^1$H NMR (in dimethylsulfoxide-$d_6$ (DMSO-$D_6$) at 400 megahertz (MHz)) indicated that both samples were contaminated with 4-methoxy cinnamoyl chloride. Pure material could be produced by recrystallization from dry hexane.

Synthesis of 6-Methyl-3-Chlorobenzo[b]thiophene-2-Carbonyl Chloride

A 250 ml, 3-necked, round bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and allowed to cool to room temperature. The reaction flask was charged with 4-methylcinnamic acid (Aldrich, 20 g, 123.31 mmole), anhydrous pyridine (Aldrich, 2.2 ml, 27.28 mmole), anhydrous dimethylformamide (Aldrich, 4.4 ml, 56.82 mmole) and anhydrous chlorobenzene (Aldrich, 20 ml) at room temperature. At this point the apparatus was disconnected from the dry nitrogen source.

Thionyl chloride (Aldrich, 451.32 mmole, 39.1 ml) was added to the reaction mixture in a dropwise fashion by means of a syringe, over a period of 20 minutes. Evolution of hydrogen chloride was observed, together with the rapid dissolution of the white solid in the flask to give a yellow-brown solution. Upon completion of addition, the reaction mixture was rapidly stirred at room temperature for 30 minutes and then heated by means of a heating mantle to reflux for 16 hours. Upon cooling the reaction mixture to room temperature, the dark brown solution solidified.

The contents of the flask were broken into small pieces, slurried and transferred to a 1000 ml Erlenmeyer flask using hot, dry hexane (1000 ml, dried over magnesium sulfate, 25 g/1000 ml). The hot hexane slurry was heated to boiling for 30 minutes during which time, most of the residue gradually dissolved. The resulting orange-yellow hot hexane solution was decanted off from the remaining residue and concentrated to 750 ml. The solution was allowed to cool to room temperature, and then stored at 4° C. overnight. This resulted in a yellow precipitate, which was filtered off and dried in vacuo, to give 19.46 g of the desired material. $^1$H NMR (DMSO-$D_6$, 400 MHz) indicated that the recovered material was predominantly the desired material (a purity of greater than 95% was determined by NMR).

Preparation of 6-Methoxy-7,3-Dichlorobenzo[b]thiophene-2-Carbonyl Chloride

A 100 ml, 3-necked, round bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and cooled to room temperature. The reaction flask was charged with 4-methoxycinnamic acid (Aldrich,10 g, 60 mmole), anhydrous pyridine (Aldrich, 1 ml, 12.4 mmole), anhydrous dimethylformamide (Aldrich, 2.0 ml, 25.8 mmole) and anhydrous chlorobenzene (Aldrich, 10 ml) at room temperature. At this point the apparatus was disconnected from the dry nitrogen source.

Thionyl chloride (Aldrich, 205.6 mmole, 15 ml) was added to the reaction mixture in a dropwise fashion by means of a syringe, over a period of 10 minutes. Evolution of hydrogen chloride was observed, together with the rapid dissolution of the white solid in the flask to give a yellow-brown solution. Upon completion of addition, the reaction mixture was rapidly stirred at room temperature for 30 minutes and then the mixture was heated by means of a heating mantle to a temperature of 140°–145° C. for 6 days. Upon cooling the reaction mixture to room temperature, the dark brown solution solidified.

The contents of the flask were broken into small pieces, slurried and transferred to a 500 ml Erlenmeyer flask using hot, dry hexane (500 ml, dried over magnesium sulfate, 25 g/1000 ml). The hot hexane slurry was heated to boiling for 30 minutes during which time, most of the residue gradually dissolved. The resulting orange-yellow hot hexane solution was decanted from the remaining residue and the solution was concentrated to 350 ml. The solution was cooled to room temperature, and then stored at 4° C. overnight. A yellow precipitate formed during the cooling, which was filtered off, and dried in vacuo, to give 2.25 g of the desired material. Further concentration of the filtrate to 200 ml and repeating the above described crystallization steps yielded an additional 1.20 g.

Preparation of 6-Methoxy-7-Chlorobenzo[b]thiophene-2-Carbonyl Chloride

A 100 ml, 3-necked, round bottomed flask, reflux condenser, thermometer adapter, gas inlet and Teflon stirrer were oven dried for 12 hours at 160° C. The apparatus was rapidly assembled, fitted with a thermometer, flushed with dry nitrogen gas, sealed with rubber septa and cooled to room temperature. The reaction flask was charged with 4-methoxycinnamic acid (Aldrich,10 g, 60 mmole), anhydrous pyridine (Aldrich, 1 ml, 12.4 mmole), anhydrous dimethylformamide (Aldrich, 2.0 ml, 25.8 mmole) and anhydrous chlorobenzene (Aldrich, 100 ml) at room temperature. At this point the apparatus was disconnected from the dry nitrogen source.

Thionyl chloride (Aldrich, 480 mmole, 35 ml) was added to the reaction mixture in a dropwise fashion by means of a syringe, over a period of 10 minutes. Evolution of hydrogen chloride was observed, together with the rapid dissolution of the white solid in the flask to give a yellow-brown solution. Upon completion of addition, the reaction mixture was rapidly stirred at room temperature for 30 minutes and then heated by means of a heating mantle to a temperature of 140°–145° C. for 6 days. Upon allowing the reaction mixture to cool to room temperature, the dark brown solution solidified.

The excess thionyl chloride and chlorobenzene was removed by distillation at reduced pressure. Upon completion of the distillation, the contents of the flask were broken-up into small pieces, slurried and transferred to a 500 ml Erlenmeyer flask using hot, dry hexane (500 ml, dried over magnesium sulfate, 25 g/1000 ml). The hot hexane slurry was heated to boiling for 30 minutes during which time, most of the residue gradually dissolved. The resulting orange-yellow hot hexane solution was decanted from the remaining residue and concentrated to 350 ml. The solution was cooled to room temperature, and then stored at 4° C. overnight. A yellow precipitate formed which was filtered off, and dried in vacuo, to give 1.25 g of the 7-chloro [b]benzothiophene.

General Preparation of Methyl, Ethyl and Isopropyl Esters from Aryl or Heteroaryl Acyl Chlorides The corresponding carboxylic acid (10 mmoles) was transferred to a 100 ml round bottomed flask. Anhydrous methanol (Aldrich, 50 ml) was added and the acid dissolved by stirring. To this stirred solution was added chlorotrimethylsilane ($Si(CH_3)_3Cl$, 2.5 equivalents, 25 mmole). The reaction mixture was stirred at room temperature and monitored by TLC (Silica, 1:1 hexane:ethyl acetate, and 100% ethyl acetate, iodine stain and UV visualization). Upon completion of the reaction as determined by TLC analysis (16–48 hours at room temperature), the resulting solution was concentrated in vacuo to give crude material, which was shown by $^1H$ NMR (DMSO-$D_6$, 400 MHz) to be the desired material in a high level of purity. The crude methyl ester can be used directly or recrystallized from a suitable solvent (e.g., methanol, ethanol or acetonitrile).

The preparation of the corresponding ethyl and isopropyl esters was accomplished using the same technique, but ethanol or isopropyl alcohol was substituted for methanol respectively.

Preparation of Methyl 6-Methoxy-3-Chlorobenzo[b] thiophene-2-Carboxylate

Crude 6-methoxy-3-chlorobenzo[b]thiophene-2-carbonyl chloride (2 g, 7.67 mmoles) was transferred to a 100 ml round bottomed flask. Anhydrous methanol (Aldrich, 50 ml) was added and the acid chloride dissolved by stirring. To this stirred solution was added chlorotrimethylsilane (2.5 equivalents, 19.16 mmole, 2.08 g, 2.43 ml). The reaction mixture was stirred overnight at room temperature. TLC analysis (Silica, 1:1 hexane:ethyl acetate, UV visualization) indicated complete conversion of the acid chloride to the methyl ester. The resulting slurry was concentrated in vacuo to give a yellow solid, which was shown by $^1H$ NMR (DMSO-$D_6$, 400 MHz) to be the desired material. The crude methyl ester was dissolved in hot ethanol (200 ml), the volume was reduced to 150 ml, and allowed to cool to room temperature. The resulting orange ethanolic solution was cooled to −10° C. for 15 minutes. The resulting precipitate was filtered off and dried in vacuo to give 1.25 g of the ester as an off-white solid.

Preparation of Methyl 6-Methyl-3-Chlorobenzo[b] thiophene-2-Carboxylate

Crude 6-methyl-3-chlorobenzo[b]thiophene-2-carbonyl chloride (5 g, 20.46 mmoles) was transferred to a 250 ml round bottomed flask. Anhydrous methanol (Aldrich, 80 ml) was added and the acid chloride dissolved by stirring. To this stirred solution was added chlorotrimethylsilane (3.0 equivalents, 61.38 mmole, 6.68 g, 7.80 ml). The reaction mixture was stirred at room temperature and the progress of the reaction monitored by TLC (Silica, 1:1 hexane:ethyl acetate, and 100% ethyl acetate, iodine and UV visualization). The reaction was shown to be complete after 24 hours. The resulting slurry was concentrated in vacuo to give 4.80 g of a yellow solid, which was shown by $^1H$ NMR (DMSO-$D_6$, 400 MHz) to be the desired material. The crude methyl ester was shown to be pure and used directly.

General Method for the Preparation of Aryl and Heteroaryl Hydrazides from Aryl and Heteroaryl Esters A 100 ml bottomed flask, reflux condenser, gas inlet and Teflon stirrer were oven dried for 12 hours at 160° C. The apparatus was rapidly assembled, flushed with dry nitrogen gas, and allowed to cool to room temperature. The reaction flask was charged with methyl ester (5.0 mmole), anhydrous methanol (Aldrich, 50 ml), and anhydrous hydrazine (Aldrich, 2.5 equivalents, 12.5 mmole). The stirred reaction mixture was brought to reflux and the progress of the reaction monitored by TLC (Silica, 1:1 hexane:ethyl acetate, and 100% ethyl acetate, iodine and UV visualization). Upon completion of the reaction, the reaction mixture was cooled to room temperature, and further cooled to 5° C. for 1 hour. The resulting solid was filtered off, washed with cold methanol (2×10 ml), and dried in vacuo. The resulting hydrazide was sufficiently pure to be used directly.

General Method for the Preparation of Aryl and Heteroaryl Hydrazides from Aryl and Heteroaryl Acyl or Sulfonyl Chlorides A 250 ml, 3-necked round bottomed flask, Teflon stirrer, 50 ml pressure equalized addition funnel, and gas inlet were oven dried for 12 hours at 160° C. The apparatus was rapidly assembled, flushed with dry nitrogen gas, and cooled to room temperature. The reaction flask was charged with anhydrous THF (Aldrich, 100 ml) and anhydrous hydrazine (Aldrich, 131.0 mmole, 4.21 g, 4.12 ml). The reaction mixture was cooled to 0° C. (ice/water), and a THF solution (20 ml) of 2-naphthoyl chloride (10 g, 52.54 moles) was added over 30 minutes in a dropwise fashion to the stirred reaction mixture. Upon completion of addition, the reaction mixture was warmed to room temperature and stirred overnight. The reaction mixture was poured onto ice/water (1000 ml), and vigorously stirred for 1 hour. The resulting white slurry was filtered, washed with cold water (4×50 ml), and dried in vacuo to give 9.80 g of a white powder. $^1H$ NMR (DMSO-$D_6$, 400 MHz) showed the product to be pure.

Preparation of 6-Methoxy-3-Chlorobenzo[b]thiophene-2-Hydrazide

A 100 ml, round bottomed flask, reflux condenser, gas inlet and Teflon stirrer were oven dried for 12 hours at 160° C. The apparatus was rapidly assembled, flushed with dry nitrogen gas, and cooled to room temperature. The reaction flask was charged with methyl 6-methoxy-3-chlorobenzo[b] thiophene-2-carboxylate (1.50 g, 5.85 mmole), anhydrous methanol (Aldrich, 50 ml), and anhydrous hydrazine (Aldrich, 2.5 equivalents, 0.47 g, 0.45 ml, 14.61 mmole). The stirred reaction mixture was brought to reflux and the progress of the reaction monitored by TLC (Silica, 1:1 hexane:ethyl acetate, and 100% ethyl acetate, iodine and UV visualization). After 72 hours, the completed reaction was cooled to room temperature, and further cooled to 5° C. for 1 hour. The resulting solid was filtered, washed with cold methanol (2×10 ml), and dried in vacuo. This resulted in 0.856 g of the desired material, as a white amorphous powder which was used directly.

Preparation of 3-Chlorobenzo[b]thiophene-2-Carboxy-2'-[(2,5-Dichlorophenylamino)thia]hydrazine, Compound XVIII A 50 ml round bottomed flask, Teflon stirrer and gas inlet were oven dried for 12 hours at 160° C. The apparatus was flushed with dry nitrogen and cooled. The reaction flask was charged with 3-chlorobenzo[b]thiophene-2-carboxyhydrazide (2 g, 8.85 mmole), which was dissolved with anhydrous tetrahydrofuran (THF, 25 ml). To this homogeneous reaction mixture was added 2,5-dichlorophenyl isothiocyanate (1.88 g, 9.2 mmole) in anhydrous THF (4 ml). The reaction mixture was stirred at room temperature for 24 hours. The resulting slurry was diluted with anhydrous THF (10 ml), and stirred for a further 10 minutes. The solid was filtered off, washed with 1:1 hexane-diethyl ether (15 ml), and dried in vacuo to give 1.21 g of pure product.

Preparation of 3-Chlorobenzo[b]thiophene-2-Carboxy-2'-[(3,4-Dichlorophenylamino)oxa]hydrazine A 50 ml round bottomed flask, Teflon stirrer and gas inlet were oven dried for 12 hours at 160° C. The apparatus was flushed with dry nitrogen and cooled. The reaction flask was charged with 3-chlorobenzo[b]thiophene-2-carboxyhydrazide (2 g, 8.85 mmole), which was dissolved with anhydrous THF (25 ml). 3,4-Dichlorophenyl isocyanate (1.73 g, 9.2 mmole) in anhydrous THF (4 ml) was added in one lot to the stirred homogeneous reaction mixture. The reaction mixture was stirred at room temperature for 24 hours. The resulting slurry was diluted with anhydrous THF (10 ml), and stirred for a further 10 minutes. The solid was filtered, washed with 1:1 hexane-diethyl ether (15 ml), and dried in vacuo to give 1.21 g of pure product.

2. Synthesis of Compounds XI–XLV

The following General Procedures illustrate the synthesis of the compounds in the class defined by the structure of Compound XI.

General Procedure A: Synthesis of 5-Dimethoxymethyl-3-Cyano-2-Thioetherpyridines and Pyrido[b]thiophenes The following demonstrates the synthesis of Compound 8 of Scheme 2. Into a round-bottom flask equipped with a magnetic stir bar and under a positive pressure of nitrogen were placed 3-cyano-2-mercaptopyridine-6-carboxaldehyde dimethyl acetal (1.0513 g 5.0 mmol), DMF (5 ml), $K_2CO_3$ (0.7602 g, 5.5 mmol), and the corresponding alkylating agent (5.2 mmol). The heterogeneous mixture was stirred at room temperature for 3 hr. The reaction mixture was poured into ice/$H_2O$ (50 ml) and extracted twice with ethyl acetate (EtOAc.) The combined organic layers were washed with saturated sodium chloride (NaCl, brine), dried over magnesium sulfate ($MgSO_4$), filtered, and the solvent removed by rotary evaporation to yield the coupled product. Isolated yields range from 87–96% The product was analyzed by $^1H$ NMR and TLC.

General Procedure B: Acetal Deprotection of 5-Dimethoxymethyl-3-Cyano-2-Thioetherpyridines and Pyrido[b]thiophenes The following demonstrates the conversion of Compound 8 of Scheme 2 into Compound 9 of the same Scheme. Into a round-bottom, three-necked flask equipped with a magnetic stir bar, thermometer, reflux condenser, and under a positive pressure of nitrogen, were placed the corresponding dimethyl acetal (5.0 mmol), benzcile (60 ml), and p-toluenesulfonic acid (1.9975 g, 10.5 mmol). The mixture was refluxed at 73°–78° C. for 48 hours (h). The reaction was quenched by pouring the reaction mixture into saturated aqueous (sat. aq.) sodium bicarbonate ($NaHCO_3$) and then extracted twice with methylene chloride. The combined organic layers were washed with sat. NaCl (brine), dried over $MgSO_4$, filtered, and the solvent removed by rotary evaporation to yield the desired aldehyde. The product was analyzed by $H^1$ NMR and TLC.

General Procedure C: Synthesis of 5-Iminio-3-Cyano-2-Thioetherpyridines and Pyrido[b]thiophenes This procedure demonstrates the conversion of Compound 8 or Compound 9 of Scheme 2 into Compound 10 of that Scheme. Into a round bottom, three-necked flask equipped with a magnetic stir bar, thermometer, reflux condenser, and under a positive pressure of nitrogen, were placed the corresponding dimethyl acetal or aldehyde (1.0 mmol), 3Å molecular sieves (5.0 g), benzene (12 ml), and p-toluenesulfonic acid (0.3995 g, 2.1 mmol), and the amine (1.0 mmol). The mixture was refluxed at 73°–78° C. for 24–48 h. Upon cooling, the molecular sieves where filtered off and washed with methylene chloride. The filtrate was poured into sat. aq. $NaHCO_3$ and extracted twice with methylene chloride. The combined organic layers were washed with sat. NaCl (brine), dried over $MgSO_4$ (or sodium sulfate ($Na_2SO_4$)), filtered, and the solvent removed by rotary evaporation to yield the crude product. The crude product was recrystallized from acetonitrile. The final product was analyzed by $^1H$ NMR and TLC.

General Procedure D: Deprotection of Dimethoxyacetal Pyridine Thioethers

This procedure also illustrates the conversion of compound 8 of Scheme 2 into compound 9 of that Scheme. Into a round bottom, three-necked flask equipped with a magnetic stir bar, thermometer and under a positive nitrogen pressure, were introduced the corresponding acetal (7.0 mmol) and chloroform ($CHCl_3$, 63 mL). To this mixture a second mixture of aqueous trifluoroacetic acid (TFA/$H_2O$, 31 mL/31 mL) at 0° C. The mixture was stirred vigorously at 35° C. until completion, as determined by TLC analysis (3–78 h.) The reaction was quenched with sat. aq. $NaHCO_3$ and the solution extracted twice with EtOAc. The organic layers from each extraction were combined and washed with sat. aq. NaCl (brine), then dried over sodium sulfate ($Na_2SO_4$) and filtered. The solvent was removed by rotary evaporation, and the product analyzed by $^1H$ NMR and TLC.

General Procedure E: Synthesis of Hydrazide and Semicarbazide Derivatives

This procedure illustrates the formation of compound 11 of Scheme 2. Into a reaction vessel equipped with a magnetic stir bar, were placed the corresponding dimethyl acetal (0.25 mmol), semicarbazide or hydrazide (0.25 mmol), methanol (2.5 mL), and 2 drops of concentrated hydrochloric acid (HCl.) The vessel was sealed with a rubber septa and provided with a pressure release needle. The vessel was placed in a sonicator and heated to 50° C. for two days. Upon cooling, the solids were isolated by filtration and washed with methanol. The product was dried overnight in a high vacuum oven.

The application of the above-described General Procedures to the syntheses of certain compounds of the invention is illustrated in Table 4 below. As noted above, the details of applying the General Procedures to the synthesis of the individual compounds of the invention can be performed using standard methods and materials.

TABLE 4

| Compound | Methods | Compound | Methods |
| --- | --- | --- | --- |
| XII | A, C | XXX | A, C |
| XIII | A, C | XXXI | A, C |
| XVI | A, C | XXXII | A, D, C |
| XVII | A, C | XXXIII | A, C |
| XVIII | A, C | XXXIV | A, D, C |
| XIX | A, C | XXXV | A, D, C |
| XX | A, C | XXXVI | A, C |
| XXI | A, C | XXXVII | A, C |
| XXII | A, C | XXXVIII | A, C |
| XXIII | A, C | XXXIX | A, C |
| XXIV | A, C | XLI | A, B |
| XXV | A, C | XLII | A, B |
| XXVI | A, C | XLIV | A, C |
| XXVII | A, C | XLV | A, C |
| XXVIII | A, C | XLVII | A, E |
| XXIX | A, C | XLVIII | A, E |

B. Anti-tumor Activity
  1. Ex vivo Studies
  a. Reduction of Telomere Length in Tumor Cells Colonies of the ovarian tumor cell lines OVCAR-5 and SK-OV-3 and normal human BJ cells (used as a control) were prepared using standard methods and materials. In one test, the colonies were prepared by seeding 15-centimeter dishes with about $10^6$ cells in each dish. The dishes were incubated to allow the cell colonies to grow to about 80% confluence, at which time each of the colonies was divided into two groups. One group was exposed to a subacute dose of Compound XVIII (10 µM) 4–8 hours after plating following the split; the other group was exposed to a DMSO control.

Each group was then allowed to continue to divide, and the groups were split evenly again (near confluence). The same number of cells were seeded for continued growth. The compound or control was added every fourth day to the samples at the same concentration delivered initially (10 µM). Remaining cells were analyzed for telomere length. As the untested cell cultures neared confluence, the samples were split again as just described. This sequence of cell doubling and splitting was continued for 20–25 doublings. Thus, a determination of telomere length as a function of cell doublings was obtained.

Telomere length was determined by digesting the DNA of the cells using restriction enzymes specific for sequences other than the repetitive $T_2AG_3$ sequence of human telomeres. The digested DNA was separated by size using standard techniques of gel electrophoresis to determine the lengths of the telomeric repeats, which appeared, after probing, on the gel as a smear of high-molecular weight DNA (approximately 2 Kb–15 Kb).

The results of the telomere length analysis indicated that the test compound of the invention had no affect on the rate of decrease in telomere length for BJ (control) cells as a function of progressive cell doublings. With respect to the tumor cell lines, however, measurable decreases in telomere length were determined in as few as eight doublings for tumor cells exposed to the test compound of the invention. Tumor cells exposed to the control maintained steady telomere lengths as expected. Thus, Compound XVIII was demonstrated to cause resumption of the normal loss of telomere length as a function of cell division in tumor cells.

In another experiment, HEK-293 cells were incubated with Compound XVIII and a DMSO control at concentrations of 3.2 µM and 10 µM using the protocol just described. Cells were observed to enter crisis (i.e., the cessation of cell function) within 12 weeks following administration of Compound XVIII at 10 µM and after 16 weeks in the case where Compound XVIII was administered at a concentration of 3.2 µM. In addition, TRF analyses of the cells using standard methodology showed that the test compound caused reductions in telomere length by 350 bp and 330 bp, respectively. No cytotoxic effects were observed.

b. Specificity

Compound XVIII was screened for activity ($IC_{50}$) against telomerase and several enzymes having nucleic acid binding or modifying activities related to telomerase using standard techniques. The enzymes screened included Telomerase, DNA Polymerase I, HeLa RNA Polymerase II, T3 RNA Polymerase, MMLV Reverse Transcriptase, Topoisomerase I, Terminal Transferase and Single-Stranded DNA Binding Protein (SSB). Compound XVIII was also found to have high specificity for telomerase as compared to Glucose-6-Phosphate Dehydrogenase. The test compound was found to have an $IC_{50}$ of 30 µM with respect to telomerase and an $IC_{50}$ of 100 µM with respect to SSB. No significant inhibition was observed with respect to any of the remaining enzymes. Thus, Compound XVIII demonstrated high specificity for telomerase.

c. Cytotoxicity

The MTT assay for cytotoxicity was performed using the ovarian tumor cells lines OVCAR-5 and SK-OV-3. Cells from the normal human cell line BJ were used as a control. The cell lines used in the assay were exposed to Compound XVIII of the invention for 72 hours at concentrations ranging from 3 µM to 1,000 µM. During this period, the optical density (OD) of the samples was determined for light at 540 nanometers (nm). No significant cytotoxic effects were observed at concentrations less than about 15 µM.

2. In vivo Studies

A human tumor xenograft model in which OVCAR-5 tumor cells are grafted into nude mice can be constructed using standard techniques and materials. The mice are divided into two groups. One group is treated intraperitoneally with Compound XVIII. The other group is treated with a control comprising a mixture of either DMSO or ethanol and emulphor (oil) and phosphate buffer solution (PBS). The average tumor mass for mice in each group is determined periodically following the xenograft using standard methods and materials.

In the group treated with a compound of the invention (e.g., Compound XVIII), the average tumor mass is expected to increase following the initial treatment for a period of time, after which time the tumor mass is expected to stabilize and then begin to decline. Tumor masses in the control group are expected to increase throughout the study. Thus, the compounds of the invention are expected to lessen dramatically the rate of tumor growth and ultimately induce reduction in tumor size and elimination of the tumor.

Thus, the present invention provides novel compounds, compositions and methods for inhibiting telomerase activity and treating disease states in which telomerase activity has deleterious effects, especially cancer. The compounds of the invention provide a highly selective and effective treatment for malignant cells that require telomerase activity to remain immortal; yet, without affecting non-malignant cells.

Although certain embodiments and examples have been used to describe the present invention, it will be apparent to those of skill in the art that changes may be made to those described embodiments and examples without departing from the scope or spirit of the invention or the following claims.

What is claimed:

1. A telomerase inhibiting compound comprising the structure:

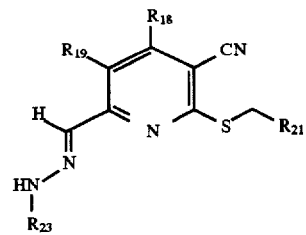

and its pharmaceutically acceptable salts, wherein:

$R_{21}$ is selected from the group consisting of aryl, aralkyl, alkylcarbonyl, arylcarbonyl, aralkylcarbonyl, aminocarbonyl, alkylaminocarbonyl, arylaminocarbonyl, dialkylaminocarbonyl, diarylaminocarbonyl, arylalkylaminocarbonyl, carboxyl, alkoxycarbonyl, aryloxycarbonyl, sulfo, alkylsulfonyl and arylsulfonyl;

$R_{18}$ and $R_{19}$ are selected independently from the group consisting of hydrogen, halogen, hydroxy, aryloxy, alkoxy, lower alkyl; and $R_{23}$ is selected from the group consisting of hydrogen, alkyl, aryl, and aralkyl.

2. The compound of claim 1, wherein $R_{21}$ is aryl.

3. The compound of claim 2, wherein $R_{23}$ is aryl.

4. The compound of claim 3 having the structure:

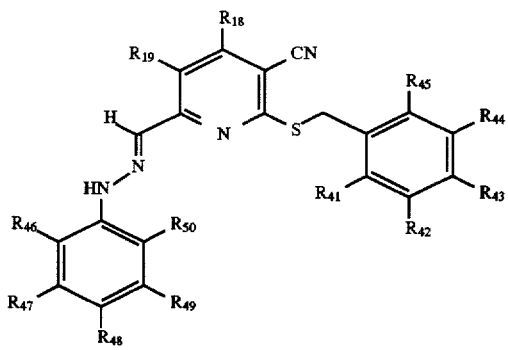

wherein $R_{41}$–$R_{50}$ are selected independently from the group consisting of hydrogen, halogen, hydroxyl, amino, alkylamino, arylamino, dialkylamino, diarylamino, arylalkylamino, lower alkyl, alkoxyl, nitro and cyano.

5. The compound of claim 4, wherein $R_{41}$–$R_{45}$ are selected independently from the group consisting of hydrogen and halogen; and $R_{46}$–$R_{50}$ is selected independently from the group consisting of hydrogen, halogen and lower alkyl.

6. The compound of claim 5, wherein $R_{41}$, $R_{42}$, $R_{45}$–$R_{47}$, $R_{49}$ and $R_{50}$ are hydrogen, $R_{43}$ and $R_{44}$ are chloro and $R_{48}$ is chloro.

7. A composition for treating cancer, comprising a therapeutically effective amount of a compound of claim 1 in a pharmaceutically acceptable carrier.

8. A method of treating a cancer susceptible to a compound of claim 1 in a mammal, comprising administering to such mammal a therapeutically effective amount of compound of claim 1 to inhibit telomerase activity in cancer cells in said mammal such that the telomeres of said cancer cells are reduced in length over successive cell divisions.

9. The compound of claim 5, wherein $R_{41}$, $R_{42}$, $R_{45}$–$R_{47}$, $R_{49}$ and $R_{50}$ are hydrogen, $R_{43}$ and $R_{44}$ are chloro and $R_{48}$ is methyl.

* * * * *